(12) United States Patent
Feuerbach et al.

(10) Patent No.: US 8,173,667 B2
(45) Date of Patent: May 8, 2012

(54) 1-AZA-BICYCLOALKYL DERIVATIVES

(75) Inventors: Dominik Feuerbach, Mullheim (DE);
Mathias Frederiksen, Basel (CH);
Martin Marzi, Birsfelden (CH);
Bernard Lucien Roy, Fribourg (CH)

(73) Assignee: Novartis AG, Basel (CH)

( * ) Notice: Subject to any disclaimer, the term of this patent is extended or adjusted under 35 U.S.C. 154(b) by 410 days.

(21) Appl. No.: 12/090,931

(22) PCT Filed: Oct. 19, 2006

(86) PCT No.: PCT/EP2006/010099
§ 371 (c)(1),
(2), (4) Date: Apr. 21, 2008

(87) PCT Pub. No.: WO2007/045478
PCT Pub. Date: Apr. 26, 2007

(65) Prior Publication Data
US 2008/0255135 A1  Oct. 16, 2008

(30) Foreign Application Priority Data
Oct. 21, 2005 (GB) .................. 0521508.2

(51) Int. Cl.
*A61K 31/44* (2006.01)
*C07D 453/02* (2006.01)
*C07D 221/04* (2006.01)
*A61P 29/00* (2006.01)
*A61P 25/22* (2006.01)
*A61P 25/28* (2006.01)
*A61P 25/16* (2006.01)
*A61P 25/24* (2006.01)
*A61P 25/18* (2006.01)
*A61P 25/08* (2006.01)

(52) U.S. Cl. ........ 514/299; 514/305; 546/137; 546/133; 546/183; 546/112

(58) Field of Classification Search .................. 546/137, 546/133, 183, 112; 514/299, 305
See application file for complete search history.

(56) References Cited

U.S. PATENT DOCUMENTS

| | | | |
|---|---|---|---|
| 4,921,860 A | 5/1990 | Cliffe | |
| 5,385,912 A | 1/1995 | Neuenschwander et al. | |
| 5,434,161 A | 7/1995 | Becker et al. | |
| 5,494,918 A | 2/1996 | Neuenschwander et al. | |
| 5,589,477 A | 12/1996 | Chokai et al. | |
| 5,612,352 A | 3/1997 | Brown et al. | |
| 7,160,876 B2 | 1/2007 | Ji et al. | |
| 7,655,657 B2 | 2/2010 | Stoner et al. | |
| 7,674,794 B2 | 3/2010 | Ji et al. | |
| 7,713,976 B2 | 5/2010 | Feuerbach et al. | |
| 7,713,977 B2* | 5/2010 | Feuerbach et al. | 514/252.01 |
| 7,750,011 B2* | 7/2010 | Peters et al. | 514/252.02 |
| 2003/0045523 A1 | 3/2003 | Schmitt et al. | |
| 2005/0137184 A1 | 6/2005 | Ji et al. | |
| 2005/0137203 A1 | 6/2005 | Ji et al. | |
| 2005/0137204 A1 | 6/2005 | Ji et al. | |
| 2005/0137226 A1 | 6/2005 | Ji et al. | |
| 2005/0137398 A1 | 6/2005 | Ji et al. | |
| 2005/0154045 A1 | 7/2005 | Luithle et al. | |
| 2005/0209236 A1 | 9/2005 | Hendrix et al. | |
| 2005/0215571 A1 | 9/2005 | Romano | |
| 2005/0245504 A1 | 11/2005 | Corbett et al. | |
| 2005/0245531 A1 | 11/2005 | Ji et al. | |
| 2006/0019984 A1 | 1/2006 | Groppi et al. | |
| 2006/0106096 A1 | 5/2006 | Flessner et al. | |
| 2006/0142180 A1 | 6/2006 | Shytle et al. | |
| 2006/0211686 A1 | 9/2006 | Kohlhaas et al. | |
| 2007/0037844 A1 | 2/2007 | Luithle et al. | |
| 2007/0060575 A1 | 3/2007 | Zhu et al. | |
| 2007/0060588 A1 | 3/2007 | Ji et al. | |
| 2007/0066592 A1 | 3/2007 | Ji et al. | |
| 2007/0232631 A1 | 10/2007 | Khan et al. | |
| 2007/0249657 A1 | 10/2007 | Feuerbach et al. | |
| 2008/0096891 A1 | 4/2008 | Benedetti et al. | |
| 2008/0108600 A1* | 5/2008 | Wang et al. | 514/218 |
| 2008/0194573 A1 | 8/2008 | Feuerbach et al. | |
| 2008/0262030 A1 | 10/2008 | Frederiksen et al. | |
| 2008/0293731 A1 | 11/2008 | Feuerbach et al. | |
| 2009/0054446 A1 | 2/2009 | Feuerbach et al. | |
| 2010/0093746 A1* | 4/2010 | Feuerbach et al. | 514/252.04 |
| 2010/0179160 A1 | 7/2010 | Feuerbach et al. | |
| 2010/0184775 A1 | 7/2010 | Frederiksen et al. | |
| 2011/0034475 A1 | 2/2011 | Feuerbach et al. | |

FOREIGN PATENT DOCUMENTS

CA  2042860 A1  11/1991
(Continued)

OTHER PUBLICATIONS

William H. Bunnell et al., Design of Ligands for the Nicotinic acetylcholine receptors: The Quest for Selectivity, Current Topics in Medicinal Chemistry, 2004, pp. 299-334.
Anatoly Mazurov et al., Selective a7 Nicotinic Acetylcholine Receptor Ligands, Current Medicianl Chemistry, 2006, pp. 1567-1584.
Anatoly Mazurov et al., 2-(Arylmethly)-3-substituted quinuclidines as selective a7 Nicotinic Receptor Ligands, Bioorganic & Medicinal Chemistry Letters 15, 2005, pp. 2073-2077.
Domminik Feuerbach et al., PTO Office Action/Restriction Requirement, U.S. Appl. No.11/571,536, Nov. 25, 2008, 6 pages.
Canadian Examination Report dated May 31, 2010, 3 pgs.
Dominik Feuerbach, U.S. PTO Notice of Allowance, U.S. Appl. No. 12/262,896, Jun. 16, 2010, 11 pgs.
Dominik Feuerbach, U.S. PTO Office Action, U.S. Appl. No. 11/571,536, dated Sep. 16, 2009, 27 pgs.
Abstract of WO 2004/022556, 7 pgs.

(Continued)

*Primary Examiner* — James O Wilson
*Assistant Examiner* — Cecilia M Jaisle
(74) *Attorney, Agent, or Firm* — Paul D. Strain, Esq.; Strain & Strain PLLC

(57) ABSTRACT

The present invention provides a compound of formula (I)

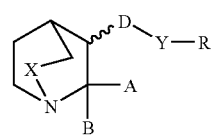

(I)

where X, R, Y, D, A and B are as defined herein.

11 Claims, No Drawings

FOREIGN PATENT DOCUMENTS

| | | |
|---|---|---|
| DE | 2 139 107 A1 | 2/1973 |
| DE | 213107 A1 | 2/1973 |
| DE | 41 16 582 A1 | 11/1991 |
| EP | 0 149 088 B1 | 7/1985 |
| EP | 0 190 920 A2 | 8/1986 |
| EP | 0 247 266 B1 | 12/1987 |
| EP | 0 287 356 A2 | 10/1988 |
| EP | 0 306 148 B1 | 3/1989 |
| EP | 0 370 415 B1 | 5/1990 |
| EP | 0 458 214 A1 | 11/1991 |
| EP | 0 560 604 B1 | 9/1993 |
| EP | 0 645 391 B1 | 3/1995 |
| GB | 2 208 385 A | 3/1989 |
| JP | 61-183223 A | 8/1986 |
| JP | 62-252764 A | 11/1987 |
| JP | 63-290878 A | 11/1988 |
| JP | 4-208267 A | 7/1992 |
| JP | 4-226981 A | 8/1992 |
| JP | 5-310732 A | 11/1993 |
| JP | 6-293768 A | 10/1994 |
| JP | 7-41463 A | 2/1995 |
| JP | 8-502481 T | 3/1996 |
| JP | 2002-30084 A | 1/2002 |
| JP | 2004-506735 A | 3/2004 |
| JP | 2005-538187 T | 12/2005 |
| JP | 2008-502642 A | 1/2008 |
| WO | WO 92/04333 A1 | 3/1992 |
| WO | WO 92/15579 A1 | 9/1992 |
| WO | WO 93/21184 A1 | 10/1993 |
| WO | WO 94/08992 A1 | 4/1994 |
| WO | WO 94/18201 A1 | 8/1994 |
| WO | WO 95/31458 A1 | 11/1995 |
| WO | WO 96/12711 A1 | 5/1996 |
| WO | WO 97/11072 A1 | 3/1997 |
| WO | WO 97/30998 A1 | 8/1997 |
| WO | WO 98/54189 A1 | 12/1998 |
| WO | WO 99/03859 A1 | 1/1999 |
| WO | WO 00/34276 A1 | 6/2000 |
| WO | WO 00/42044 A1 | 7/2000 |
| WO | WO 01/08684 A1 | 2/2001 |
| WO | WO 01/29034 A1 | 4/2001 |
| WO | WO 01/36417 A1 | 5/2001 |
| WO | WO 01/60821 | 8/2001 |
| WO | WO 01/60821 A1 | 8/2001 |
| WO | WO 01/66546 A1 | 9/2001 |
| WO | WO 01/85727 A1 | 11/2001 |
| WO | 02/15662 A2 | 2/2002 |
| WO | WO 02/16358 A2 | 2/2002 |
| WO | WO 02/20016 A1 | 3/2002 |
| WO | WO 02/085901 A1 | 10/2002 |
| WO | WO 02/100857 A1 | 12/2002 |
| WO | WO 03/037896 A1 | 5/2003 |
| WO | WO 03/043991 A1 | 5/2003 |
| WO | WO 03/051874 A1 | 6/2003 |
| WO | WO 03/072578 A1 | 9/2003 |
| WO | WO 03/078430 A1 | 9/2003 |
| WO | WO 03/078431 A1 | 9/2003 |
| WO | WO 2004/013136 A1 | 2/2004 |
| WO | WO 2004/016608 A1 | 2/2004 |
| WO | WO 2004/022556 A1 | 3/2004 |
| WO | WO 2004/029050 A1 | 4/2004 |
| WO | WO 2004/039321 A2 | 5/2004 |
| WO | WO 2004/039366 A1 | 5/2004 |
| WO | WO 2004/039815 A2 | 5/2004 |
| WO | WO 2004/043960 A | 5/2004 |
| WO | WO 2004/064836 A2 | 8/2004 |
| WO | WO 2004/076449 A2 | 9/2004 |
| WO | WO 2005/066166 A2 | 7/2005 |
| WO | WO 2005/066167 A2 | 7/2005 |
| WO | WO 2005/082340 A2 | 9/2005 |
| WO | WO 2005/111033 A2 | 11/2005 |
| WO | WO 2005/123732 A1 | 12/2005 |
| WO | WO 2006/005608 A1 | 1/2006 |
| WO | WO 2006/040352 A1 | 4/2006 |
| WO | WO 2006/048294 A1 | 5/2006 |
| WO | WO 2006/065233 A1 | 6/2006 |
| WO | WO 2006/101745 A2 | 9/2006 |
| WO | WO 2006/111662 A2 | 10/2006 |
| WO | WO 2007018738 A2 | 2/2007 |
| WO | WO 2007/068475 A1 | 6/2007 |
| WO | WO 2007/068476 A1 | 6/2007 |
| WO | WO 2007/133155 A1 | 11/2007 |

OTHER PUBLICATIONS

Perl et al., "The α7 nicotinic acetylcholine receptor in schizophrenia: decrease mRNA levels in peripheral blood lymphocytes", The FASEB Journal express article 10.1096/fje, Published online Aug. 1, 2003, 15 pgs.

Bitner et al., "Selective α7 nicotinic acetylcholine receptor activation regulates glycogen synthase kinase3β and decreases tau phosphorylation in vivo", Brain Research, vol. 1265 (2009), 10 pgs.

De Simone et al., "Activation of α7 nicotinic acetylcholine receptor by nicotine selectively up-regulates cyclooxygenase-2 and prostaglandin $E_2$ in rat microglial cultures", Journal of Neuroinflammation, vol. 2, No. 4 (2005), 10 pgs.

Jeffrey D. Schmitt, "Exploring the Nature of Molecular Recognition in Nicotinic Acetylcholine Receptors", Current Medicinal Chemistry, vol. 7, No. 8 (2000), pp. 749-800.

Holladay et al., "Neuronal Nicotinic Acetylcholine Receptors as Targets for Drug Discovery", Journal of Medicinal Chemistry, vol. 40, No. 26 (1997), pp. 4169-4194.

Toma et al., "Neuronal nicotinic acetylcholine receptor agonists", Expert Opinion on Therapeutic Patents, Vol. 14, No. 7 (2004), pp. 1029-1040.

Mullen et al., "(−)-Spiro[1-azabicyclo[2.2.2]octane-3,5'-oxazolidin-2'-one], a Conformationally Restricted Analogue of Acetylcholine, Is a Highly Selective Full Agonist at the α7 Nicotinic Aceylcholine Receptor", Journal of Medicinal Chemistry, vol. 43, No. 22 (2000), pp. 4045-4050.

Dolle et al., "Synthesis and preliminary evaluation of a carbon-1 1-labelled agonist of the α7 nicotinic acetylcholine receptor", Journal of Labelled Compounds and Radiopharmaceuticals, vol. 44, No. 11 (2001), pp. 785-795.

Tonder et al., "An improved nicotinic pharmacophore and a stereoselective CoMFA-model for nicotinic agonists acting at the central nicotinic acetylcholine receptors labeled by [$^3$H]-N-methylcarbamylcholine", Journal of Computer-Aided Molecular Design, vol. 15, No. 3 (2001), pp. 247-258.

Olesen et al., "Bioisosteric Replacement Strategy for the Synthesis of 1-Azacyclic Comounds With High Affinity for the Central Nicotinic Cholinergic Receptors", Bioorganic & Medicinal Chemistry, vol. 8, No. 6 (2000), pp. 1443-1450.

Tonder et al., "Improving the Nicotinic Pharmacophore with a Series of (Isoxazole)methylene-1-azacyclic Compounds: Synthesis, Structure-Activity Relationship, and Molecular Modeling", Journal of Medicinal Chemistry, vol. 42, No. 24 (1999), pp. 4970-4980.

Schmitt et al., "Molecular Recognition in Nicotinic Acetylcholine Receptors: The Importance of π- Cation Interactions", Journal of Medicinal Chemistry, vol. 42, No. 16 (1999), pp. 3066-3074.

CO Office Action dated Feb. 17, 2010 and English translation thereof, 15 pgs.

CO Office Action dated Feb. 22, 2010 and English translation thereof, 12 pgs.

U.S. Appl. No. 12/638,880, filed Dec. 15, 2009, Feuerbach et al.

Gillette et al., "Role of the $M_1$ receptor in regulating circadian rhythms", Life Sciences, vol. 68 (2001), pp. 2467-2472.

Hardouin et al., "Altered Cardiovascular Reponses in Mice Lacking the $M_1$ Muscarinic Acetylcholine Receptor", The Journal of Pharmacology and Experimental Therapeutics, vol. 301, No. 1 (2002), pp. 129-137.

Sheardown, "Muscarinic $M_1$ receptor agonists and $M_2$ receptor antagonists as therapeutic targets in Alzheimer's disease", Expert Opin. Ther. Patents, vol. 12, No. 6 (2002), pp. 863-870.

Kitagawa et al., "Safety, Pharmacokinetics, and Effects on Cognitive Function of Multiple Doses of GTS-21 in Healthy, Male Volunteers", Neuropsychopharmacology, vol. 28 (2003), pp. 542-551.

Plummer III et al, "Expression of the α7 nicotinic acetylcholine receptor in human lung cells", Respiratory Research (2005) 6:29, pp. 1-9.

Lubin et al., "Ultrastructural Immunolocalization of the α7 nAChR Subunit in Guinea Pig Medial Prefrontal Cortex", Annals New York Academy of Sciences (1999), pp. 628-632.

Salamone et al., "Aberrations in Nicotinic Acetylcholine Receptor Structure, Function, and Expression: Implications in Disease", McGill Journal of Medicine, vol. 5, No. 2 (2000), pp. 90-97.

Kalamide et al., "Muscle and neuronal nicotinic acetylcholine receptors Structure, function and pathogenicity", FEBS Journal, vol. 274 (2007), pp. 3799-3845.

Macor et al., "The 5-Ht$_3$ Antagonist Tropisetron (ICS 205-930) is a Potent and Selective α7 Nicotinic Receptor Partial Agonist", Bioorganic & Medicinal Chemistry Letters, vol. 11 (2001), pp. 319-321.

Glennon et al., "Central nicotinic receptor ligands and pharmacophores", Pharmaceutica Acta Helvetiae, vol. 74 (2000), pp. 103-114.

Patani et al., "Bioisosterism: A Rational Approach in Drug Design", Chem. Rev., vol. 96 (1996), pp. 3147-3176.

Dominik Feuerbach et al., U.S. PTO Notice of Allowance, U.S. Appl. No. 11/823,312, dated Apr. 7, 2009, 5 pgs.

Dominik Feuerbach et al., U.S. PTO Office Action, U.S. Appl. No. 12/262,896, dated May 27, 2009, 6 pgs.

Dominik Feuerbach et al., U.S. PTO Office Action, U.S. Appl. No. 12/262,896, dated Aug. 19, 2009, 24 pgs.

Dominik Feuerbach et al., U.S. PTO Office Action, U.S. Appl. No. 11/823,312, dated May 29, 2008, 27 pgs.

Dominik Feuerbach et al., U.S. PTO Office Action, U.S. Appl. No. 11/823,312, dated Jan. 8, 2009, 8 pgs.

Dominik Feuerbach et al., U.S. PTO Office Action, U.S. Appl. No. 11/823,312, dated Jul. 21, 2009, 3 pgs.

Dominik Feuerbach et al., U.S. PTO Office Action, U.S. Appl. No. 11/823,312, dated Mar. 10, 2008, 6 pgs.

AU Office Action dated Apr. 15, 2008, 2 pgs.

JP Office Action dated Aug. 19, 2008 and English translation, 5 pgs.

CO Office Action dated Aug. 24, 2009 and English translation, 14 pgs.

Feuerbach, U.S. PTO Notice of Allowance, U.S. Appl. No. 12/262,896, Jun. 24, 2011, 10 pgs.

Feuerbach et al., "Coupling of human nicotinic acetylcholine receptors α7 to calcium channels in GH3 cells", Neuropharmacology, vol. 48 (2005), pp. 215-227.

Michelmore et al., "Study of the calcium dynamics of the human α4β4, α3β4 and α1β1γδ nicotinic acetylcholine receptors", Naunyn-Schmiedeberg's Arch Pharmacol, vol. 366 (2002), pp. 235-245.

Feuerbach, U.S. PTO Office Action, U.S. Appl. No. 12/638,880, Jul. 19, 2011, 36 pgs.

Japanese Office Action and English translation thereof, 5 pgs, Aug. 2011.

B. Singh et al., "Immune therapy in inflammatory bowel disease and models of colitis", British Journal of Surgery, vol. 88 (2001), pp. 1558-1569.

Feuerbach, U.S. PTO Notice of Allowance, U.S. Appl. No. 12/732,646, Apr. 11, 2011, 15 pgs.

Frederiksen, U.S. PTO Office Action, U.S. Appl. No. 12/732,357, Jun. 1, 2011, 22 pgs.

Malcolm Robinson, "Medical Therapy of Inflammatory Bowel Disease for the 21st Century", Eur. J. Surg. (1998), pp. 90-98.

JP Examination Report dated May 24, 2011, 4 pgs.

"Lerneinheit: Aromatic and Saturated Heterocycles—Aromatic Five-Membered Ring Heterocycles—ChemgaPedia" [online], [retrieved on Sep. 25, 2008], retrieved from http://www.chemgapedia.de/vsengine/vlu/vsc/en/ch/12/oc/vlu_organik/het...e/vsc/en/ch/12/oc/heterocyclen/fuenfaromat/fuenfring_aromat.vscml.html, pp. 1-6.

Aboul-Enein et al, "Synthesis and antiinflammatory properties of some 1-azabicyclo [3.3.1] nonanes", European Journal of Medicinal Chemistry, Vol. 11, No. 2 (1976), pgs. 133-137.

Cahn et al., "Specification of Molecular Chirality", Angew. Chemi. Internat. Edit, vol. 5, No. 4 (1966), pp. 385-415.

CO Office Action dated Apr. 13, 2010 and English translation thereof, 7 pgs.

Court et al., "Nicotinic receptors in human brain: topography and pathology", PubMed Abstract, Journal of Chemical Neuroanatomy, vol. 20, No. 3-4 (2000), pp. 281-298.

Damaj et al. "Comparative pharmacology of nicotine and ABT-418, a new nicotinic agonist", Medline Abstract, Psychopharmacology, vol. 120, No. 4 (1995), pp. 483-490.

Damasio, "Alzheimer's Disease and Related Dementias", Cecil Textbook of Medicine, 20th Edition, vol., 2 (1996), pp. 1992-1996.

Dominik Feuerbach, U.S PTO Ex Parte Quayle Action, U.S. Appl. No. 11/570,076, Nov. 27, 2009, 10 pgs.

Dominik Feuerbach, U.S. PTO Notice of Allowance, U.S. Appl. No. 11/570,076, Jul. 20, 2010, 11 pgs.

Dominik Feuerbach, U.S. PTO Notice of Allowance, U.S. Appl. No. 12/097,681, Feb. 26, 2010, 5 pgs.

Dominik Feuerbach, U.S. PTO Notice of Allowance, U.S. Appl. No. 12/262,896, Oct. 27, 2010, 6 pgs.

Dominik Feuerbach, U.S. PTO Office Action, U.S. Appl. No. 11/570,076, Jan. 28, 2008, 28 pgs.

Dominik Feuerbach, U.S. PTO Office Action, U.S. Appl. No. 11/570,076, Oct. 23, 2007, 8 pgs.

Dominik Feuerbach, U.S. PTO Office Action, U.S. Appl. No. 11/570,076, Nov. 26, 2008, 5 pgs.

Dominik Feuerbach, U.S. PTO Office Action, U.S. Appl. No. 12/097,681, Oct. 22, 2009, 9 pgs.

Dominik Feuerbach, U.S. PTO Office Action, U.S. Appl. No. 12/097,681, Dec. 23, 2008, 19 pgs.

Dominik Feuerbach, U.S. PTO Office Action, U.S. Appl. No. 12/732,646, Sep. 28, 2010, 25 pgs.

Dominik Feuerbach, U.S. PTO Restriction Requirement, U.S. Appl. No. 12/907,506, Mar. 1, 2011, 9 pgs.

Dominik Feuerbach, U.S. PTO Supplemental Notice of Allowance, U.S. Appl. No. 12/097,681, Mar. 8, 2010, 3 pgs.

Dominik Feuerbach, U.S. PTO Restriction Requirement, U.S. Appl. No. 12/638,880, Feb. 15, 2011, 6 pgs.

Dominik Feuerbach, U.S. PTO Supplemental Notice of Allowance, U.S. Appl. No. 12/097,681, Mar. 22, 2010, 3 pgs.

Layzer, "Section Five-Degenerative Diseases of the Nervous System", Cecil Textbook of Medicine, 20th Edition, vol. 2 (1996), pp. 2050-2057.

Mathias Frederiksen, U.S. PTO Notice of Allowance, U.S. Appl. No. 12/097,689, Feb. 22, 2010, 9 pgs.

Mathias Frederiksen, U.S. PTO Office Action, U.S. Appl. No. 12/097,689, Oct. 22, 2009, 9 pgs.

Mathias Frederiksen, U.S. PTO Office Action, U.S. Appl. No. 12/097,689, Dec. 29, 2008, 18 pgs.

Mathias Frederiksen, U.S. PTO Office Action, U.S. Appl. No. 12/732,357, Sep. 28, 2010, 26 pgs.

Mathias Frederiksen, U.S. PTO Supplemental Notice of Allowance, U.S. Appl. No. 12/097,689, Mar. 19, 2010, 8 pgs.

Mirza et al., "The role of nicotinic and muscarinic acetylcholine receptors in attention", PubMed Abstract, Psychopharmacology, vol. 148, No. 3 (2000), pp. 243-250.

Terry et al., "Deficits in Spatial Learning and Nicotinic-Acetylcholine Receptors in Older, Spontaneously Hypertensive Rats", PubMed Abstract, Neuroscience, vol. 101, No. 2 (2000), pp. 357-368.

Feuerbach, U.S. PTO Office Action, U.S. Appl. No. 12/638,880, Dec. 7, 2011, 14 pgs.

Feuerbach, U.S. PTO Notice of Allowance, U.S. Appl. No. 12/732,646, Sep. 15, 2011, 9 pgs.

Burke et al., "Regionally selective cholinergic stimulation by BRL 24924 in the human isolated gut", British Journal of Clinical Pharmacology, vol. 26, No. 3 (1988), pp. 261-265.

Japanese Office Action and English translation thereof, Dec. 20, 2011, 5 pgs.

Sanger, "Increased gut cholinergic activity and antagonism of 5-hydroxytryptamine M-receptors by BRL 24924: potential clinical importance of BRL 24924", British Journal of Pharmacology, vol. 91, No. 1 (1987), pp. 77-87.

Unpublished pending U.S. Appl. No. 13/252,608, Dominik Feuerbach et al., filed Oct. 4, 2011.

* cited by examiner

1-AZA-BICYCLOALKYL DERIVATIVES

This application is the National Stage of Application No. PCT/EP2006/010099, filed on Oct. 19, 2006, which claims benefit under 35 U.S.C. § 119(a)-(d) or (f) or 365(b) of GB Application No. 05215082, filed Oct. 21, 2005, the contents of which are incorporated herein by reference in their entirety.

The present invention relates to novel 1-aza-bicycloalkyl derivatives, to processes for their production, their use as pharmaceuticals and to pharmaceutical compositions comprising them.

WO2004/022556 discloses Aza-bicycloethers and their use as nic-alpha 7 agonists. The compounds disclosed in this patent application have valuable properties, but also show disadvantages. Thus, there is a need to provide further compounds having valuable properties as nic-alpha 7 agonists.

In a first aspect, the present invention provides a compound of formula (I)

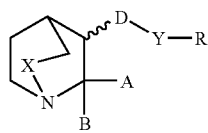

wherein
X represents $CH_2$ or a single bond;
R represents a substituted or unsubstituted $C_5$-$C_{10}$aryl or a substituted or unsubstituted $C_5$-$C_{10}$heteroaryl, or a group $N(R^1)(R^5)$, or a group $N(R^2)(CHR^3R^4)$;
Y represents a group of formula

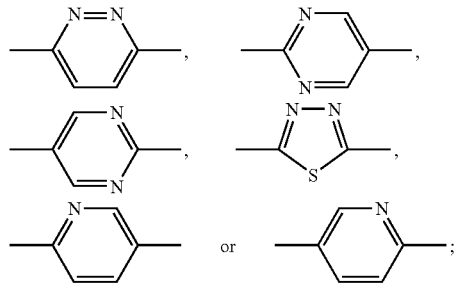

D represents NH, $NR^6$, S, S(O), $SO_2$
A and B represent, independently of each other, hydrogen or $C_1$-$C_7$alkyl under the proviso that not both A and B can represent hydrogen at the same time, or
A and B represent together with the carbon atom to which they are attached form a $C_3$-$C_7$cycloalkyl group,
$R^1$ represents hydrogen, $C_1$-$C_4$alkyl, or $CF_3$;
$R^2$ represents hydrogen, $C_1$-$C_4$alkyl, or $CF_3$;
$R^3$ represents hydrogen, $C_1$-$C_4$alkyl, or $CF_3$;
$R^4$ represents a substituted or unsubstituted $C_5$-$C_{10}$aryl or substituted or unsubstituted $C_5$-$C_{10}$heteroaryl;
$R^5$ represents a substituted or unsubstituted $C_5$-$C_{10}$aryl or substituted or unsubstituted $C_5$-$C_{10}$heteroaryl;
$R^6$ represents $C_1$-$C_4$alkyl, benzyl or benzyl substituted by one or more substituents selected from the group consisting of halogen, $C_1$-$C_4$alkyl, $C_1$-$C_4$alkoxy;
in free base or acid addition salt form.

The general terms used hereinbefore and hereinafter preferably have within the context of this disclosure the following meanings, unless otherwise indicated:

Where the plural form is used for compounds, salts, and the like, this is taken to mean also a single compound, salt, or the like.

Unless otherwise mentioned, the terms as used in this specification shall have the following meaning:

The term "unsubstituted or substituted" as used herein means that the respective radical can by substituted by one or more, preferably up to three, especially one or two substituents, especially selected from amino, $C_1$-$C_4$alkyl amino, di($C_1$-$C_4$alky)-amino, $C_3$-$C_5$cycloalkyl amino, di($C_3$-$C_5$)cycloalkyl amino, N-$C_1$-$C_4$alkyl-N-$C_3$-$C_5$cycloalkyl amino, halogen, $C_1$-$C_4$alkyl, $C_4$-$C_6$cycloalkyl, hydroxy, $C_1$-$C_4$alkoxy, $C_3$-$C_5$cycloalkyloxy, $C_1$-$C_4$alkoxy $C_1$-$C_4$alkoxy, di($C_1$$C_4$alkyl)-amino $C_1$-$C_4$alkoxy, carbamoyl, N-$C_1$-$C_4$alkyl-carbamoyl, N,N-di($C_1$-$C_4$alkyl)-carbamoyl, nitro, cyano, carboxy, $C_1$-$C_4$alkoxy carbonyl, $C_1$-$C_4$alkanoyl, $C_1$-$C_4$alkanoyloxy, benzoyl, amidino, guanidino, ureido, mercapto, $C_1$-$C_4$alkylthio, pyridyl, phenyl, phenoxy, $C_1$-$C_4$alkoxy phenyl, phenylthio, phenyl-$C_1$-$C_4$alkylthio, $C_1$-$C_4$alkylsulfonyl, phenylsulfonyl, $C_1$-$C_4$alkylphenylsulfonyl, $C_1$-$C_4$alkenyl, $C_1$-$C_4$alkanoyl, $C_1$-$C_4$alkylene dioxy bound at adjacent C-atoms of the ring, and $C_1$-$C_4$alkyl, which is substituted by halogen, hydroxy, $C_1$-$C_4$alkoxy, nitro, cyano, carboxy, $C_1$-$C_4$alkoxy carbonyl, $C_1$-$C_4$alkanoyl or $C_1$-$C_4$alkanoyloxy.

$C_5$-$C_{10}$aryl or $C_5$-$C_{10}$heteroaryl residues are to be understood as aromatic residues which are in each case unsubstituted or substituted by the substituents provided above, preferably in each case unsubstituted or substituted by one or more substituents selected from halogen, e.g. F, Cl, Br, I; CN, or alkyl, which can be unsubstituted or substituted by halogen, e.g. trifluoromethyl; or $C_1$-$C_4$alkoxy, or condensed, e.g. to a benzo[1,3]dioxole or 2,3-dihydrobenzo[1,4]dioxine and/or to a further heterocyclic ring. $C_5$-$C_{10}$heteroaryl is an aromatic heterocyclic system comprising one, two or three hetero atoms selected from N, O, S, e.g. a 5 or 7 membered aromatic heterocyclic residue optionally condensed, e.g. to 1 or 2 phenyl rings and/or to a further heterocyclic ring. Examples of $C_5$-$C_{10}$aryl or $C_5$-$C_{10}$heteroaryl residues as mentioned above include phenyl, naphthyl and isobenzofuranyl.

Alkyl is especially alkyl with from and including 1 up to and including 7, preferably from and including 1 to and including 4 C atoms, more preferably $C_1$-$C_2$alkyl, and is linear or branched; preferably, alkyl is methyl, ethyl, propyl, such as n-propyl or isopropyl, butyl, such as n-butyl, sec-butyl, isobutyl or tert-butyl, more preferably methyl or ethyl.

Alkoxy is especially $C_1$-$C_4$alkoxy, in particular methoxy, ethoxy or n-propoxy.

On account of the asymmetrical carbon atom(s) present in the compounds of formula (I) and their salts as well as the corresponding intermediates, may exist in optically active form or in form of mixtures of optical isomers, e.g. in form of racemic mixtures. All optical isomers and their mixtures including racemic mixtures, entantiomers, enantiopure diastereomers, diastereomeric mixtures are part of the present invention.

Compounds of formula (I) exist in free or acid addition salt form. In this specification, unless otherwise indicated, language such as "compounds of formula (I)" is to be understood as embracing the compounds in any form, for example free base or acid addition salt form. Salts which are unsuitable for pharmaceutical uses but which can be employed, for example, for the isolation or purification of free compounds of formula (I), such as picrates or perchlorates, are also included. For therapeutic use, only pharmaceutically acceptable salts or free compounds are employed (where applicable in the form of pharmaceutical preparations), and are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

for compounds of formula (I) and the corresponding intermediates, the following significances are preferred independently, collectively or in any combination or sub-combination:

Y preferably represents one of the following groups:

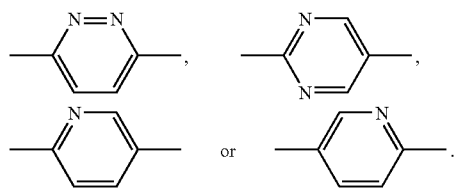

Y particularly preferably represents one of the following groups:

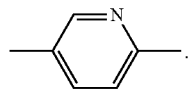

R preferably represents phenyl or substituted phenyl, the substituents being selected from the group consisting of halogen, nitro, cyano, $C_1$-$C_4$alkyl, $C_1$-$C_4$alkoxy, $C_1$-$C_4$halogenalkyl, $C_1$-$C_4$halogenalkoxy, $C_1$-$C_4$alkylsulfonyl, $C_1$-$C_4$alkylcarbonyl, $C_1$-$C_4$alkylcarbonylamino, phenyl, $C_1$-$C_4$alkylphenyl, $C_1$-$C_4$alkoxyphenyl, benzyl.

R preferably represents $C_5$-$C_{10}$ heteroaryl or substituted $C_5$-$C_{10}$ heteroaryl, the substituents being selected from the cgroup consisting of halogen, nitro, cyano, $C_1$-$C_4$alkyl, $C_1$-$C_4$alkoxy, $C_1$-$C_4$halogenalkyl, $C_1$-$C_4$halogenalkoxy, $C_1$-$C_4$alkylsulfonyl, $C_1$-$C_4$alkylcarbonyl, $C_1$-$C_4$alkylcarbonylamino, phenyl, $C_1$-$C_4$alkylphenyl, $C_1$-$C_4$alkoxyphenyl, benzyl.

R particularly preferably represents substituted phenyl, the substituents being selected from the cgroup consisting of halogen, nitro, cyano, $C_1$-$C_4$alkyl, $C_1$-$C_4$alkoxy, $C_1$-$C_4$halogenalkyl, $C_1$-$C_4$halogenalkoxy, $C_1$-$C_4$alkylsulfonyl, $C_1$-$C_4$alkylcarbonyl, $C_1$-$C_4$alkylcarbonylamino, phenyl, $C_1$-$C_4$alkylphenyl, $C_1$-$C_4$alkoxyphenyl, benzyl.

R particularly preferably represents $C_5$-$C_{10}$ heteroaryl or substituted $C_5$-$C_{10}$ heteroaryl, the substituents being selected from the cgroup consisting of halogen, nitro, cyano, $C_1$-$C_4$alkyl, $C_1$-$C_4$alkoxy, $C_1$-$C_4$halogenalkyl, $C_1$-$C_4$halogenalkoxy, $C_1$-$C_4$alkylsulfonyl, $C_1$-$C_4$alkylcarbonyl, $C_1$-$C_4$alkylcarbonylamino, phenyl, $C_1$-$C_4$alkylphenyl, $C_1$-$C_4$alkoxyphenyl, benzyl and the $C_5$-$C_{10}$ heteroaryl being selected from the group consisting of indolyl, thiophenyl, benzo[1,3]dioxolyl, furanyl, benzathiazolyl, pyrrolo[2,3-b]pyridinyl, dibenzothiophenyl, benzo[b]thiophenyl, pyridinyl, dibenzofuranyl, quinolinyl.

A preferably represents $C_1$-$C_4$alkyl, more preferably methyl or ethyl, most preferably methyl.

B preferably represents hydrogen, $C_1$-$C_4$alkyl, more preferably hydrogen, methyl or ethyl, most preferably hydrogen.

A and B preferably represent with the carbon atom to which they are attached a cycloporpyl group.

X preferably represents $CH_2$.

D preferably represents NH.

$R^1$ preferably represents H, $C_1$-$C_4$alkyl or $CF_3$.

$R^2$ preferably represents H, $C_1$-$C_4$alkyl or $CF_3$.

$R^3$ preferably represents H, $C_1$-$C_4$alkyl or $CF_3$.

$R^4$ preferably represents $C_5$-$C_{10}$aryl, which is unsubstituted or substituted by one or more substituents selected from halogen, $C_1$-$C_4$alkoxy, CN or $C_1$-$C_2$alkyl which is unsubstituted or substituted by halogen; or hetero-$C_5$-$C_{10}$aryl, which which is unsubstituted or substituted by one or more substituents selected from halogen, $C_1$-$C_4$alkoxy, CN or $C_1$-$C_2$alkyl which is unsubstituted or substituted by halogen.

$R^6$ preferably represents hydrogen, $C_1$-$C_4$alkyl or benzyl, more preferably hydrogen, methyl, ethyl or benzyl.

$R^6$ particularly referably represents Hydrogen, Methyl or Benzyl.

A preferred embodiment of the invention relates to compounds of formula (I) wherein X represent $CH_2$, R represents $C_5$-$C_{10}$aryl, which is substituted by one or more substituents selected from halogen, $NO_2$, CN, $C_1$-$C_4$alkoxy which is unsubstituted or substituted by halogen, or $C_1$-$C_4$alkyl which is unsubstituted or substituted by halogen, $C_1$-$C_4$alkylsulfonyl, $C_1$-$C_4$alkylcarbonylamino;

Y represents a group of formula

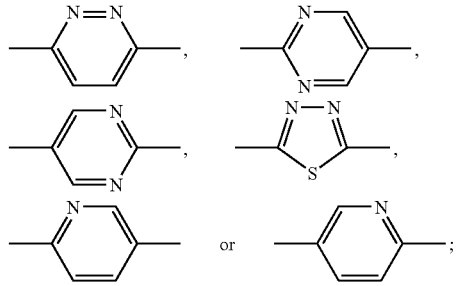

D represents NH;

A represents hydrogen or $C_1$-$C_7$alkyl and B represents hydrogen, $C_1$-$C_7$alkyl or A and B represent together with the carbon atom to which they are attached form a cyclopropyl, cyclopentyl or cyclohexyl group, A further preferred embodiment of the invention relates to compounds of formula (I) wherein X represents $CH_2$, R represents hetero-$C_5$-$C_{10}$aryl, which which is unsubstituted or substituted by one or more substituents selected from halogen, $C_1$-$C_4$alkoxy, CN or $C_1$-$C_4$alkyl which is unsubstituted or substituted by halogen, phenyl which is unsubstituted or substituted by phenyl, $C_1$-$C_4$alkoxy or benzyl;

Y represents a group of formula

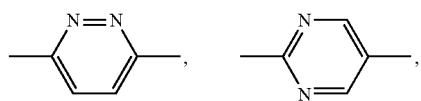

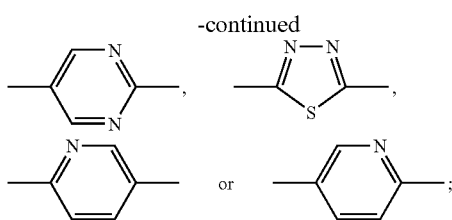

D represents NH;

A represents hydrogen or $C_1$-$C_7$alkyl and B represents hydrogen, $C_1$-$C_7$alkyl or A and B represent together with the carbon atom to which they are attached form a cyclopropyl, cyclopentyl or cyclohexyl group, Particularly preferred compounds of the invention are the compounds of the Examples.

In a further aspect, the present invention provides a processes for the production of a compound of formula (I).

A first process comprises the step of reacting a compound of formula (II)

Z-Y-R  (II)

wherein Y and R are as defined above for a compound of formula (I) and Z is a leaving group, e.g. F, Cl, Br, I or $OSO_2CF_3$, with a compound of formula (III)

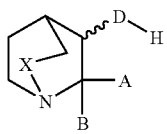  (III)

wherein A, B, D, X have the meanings as defined for a compound of formula (I), and recovering the so obtained compound of formula (I) in free base or acid addition salt form and optionally oxidizing the so obtained compound.

The above described processes for production may be carried out in accordance with standard procedures, for example as illustrated in the Examples.

Compounds of formula (II) are known or may be prepared from corresponding known compounds, e.g. as described in the Examples, e.g. in analogy to Coates W J, McKillop A (1992) Synthesis 334-342. The compounds of formula (III) are known (Vorob'eva, V. Ya.; Bondarenko, V. A.; Mikhlina, E. E.; Turchin, K. F.; Linberg, L. F.; Yakhontov, L. N. Reaction of 2-methylene-3-oxoquinuclidine with nucleophilic reagents. Khimiya Geterotsiklicheskikh Soedinenii (1977), (10), 1370-6).

Compounds of formula (III) are known or may be prepared from corresponding known compounds A second process for manufacturing the copounds of formula (I) comprises the step of reacting a compound of formula (IV)

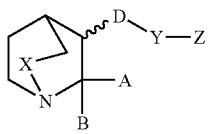  (IV)

wherein A, B, D and Y are as defined above for a compound of formula (I) and Z represents a leaving group, e.g. F, Cl, Br, I or $OSO_2CF_3$, with a compound of formula V

R-B(OH)$_2$  (V)

wherein R is as defined above for a compound of formula (I), and recovering the so obtained compound of formula (I) in free base or acid addition salt form.

Compounds of formula (IV) are novel and subject to the present invention. Compounds of formula (IV) may be prepared by reacting compounds of formula (III)

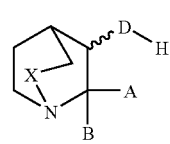  (III)

wherein A, B, D, X have the meanings as defined for a compound of formula (I), with compounds of formula (IIX)

Z-Y-Z  (IIX)

wherein Y and Z are as defined for a compound of formula (II).

In this process, reaction auxiliaries such as arylboronic acids may be used.

Compounds of formula (IIX) are known or may be prepared from corresponding known compounds.

A third process, for manufacturing the copounds of formula (I), wherein D represents NH or $NR^6$, comprises the step of reacting a compound of formula (VI)

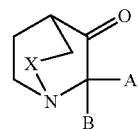  (VI)

wherein A, B and X are as defined above for compounds of formula (I) with a compound (VII)

H$_2$N-Y-R  (VII)

wherein Y and R are as defined above for compounds of formula (I) and recovering the so obtained compound of formula (I) in free base or acid addition salt form.

In this process, reaction auxiliaries, such as aryl and/or heteroarylamines may be used.

Compounds of formula (VI) are known or may be prepared from corresponding known compounds.

Compounds of formula (VII) are known or may be prepared from corresponding known compounds.

The following consideration may apply to all processes as described above, as the case may be:

Purifiacation/Isolation: Working up the reaction mixtures according to the above processes and purification of the compounds thus obtained may be carried out in accordance to known procedures.

Salt formation: Acid addition salts may be produced from the free bases in known manner, and vice-versa. Suitable acid addition salts for use in accordance with the present invention include for example the hydrochloride.

Optical pure isomers: Compounds of formula (I) in optically pure form can be obtained from the corresponding racemates according to well-known procedures, e.g. HPLC with chiral matrix. Alternatively, optically pure starting materials can be used.

Protecting groups: If one or more other functional groups, for example carboxy, hydroxy, amino, or mercapto, may need to be protected in the starting materials by protecting groups. The protecting groups employed may already be present in precursors and should protect the functional groups concerned against unwanted secondary reactions, such as acylations, etherifications, esterifications, oxidations, solvolysis, and similar reactions. It is a characteristic of protectiAng groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Oxidation: In case D represents S, an oxidation to S(O) or $SO_2$ is possible using standard oxidizing agents, e.g. $H_2O_2$, MCPBA or the like in conventional inert diluent, e.g. benzene or chlorinated solvent such as dichlormethane.

The compounds of the invention and their pharmaceutically acceptable acid addition salts, hereinafter referred to as compounds of the invention, exhibit valuable pharmacological properties when tested in vitro and in animals, and are therefore useful as pharmaceuticals.

Thus, the compounds of the invention are found to be cholinergic ligands of the nAChR. In addition preferred compounds of the invention show selective α7-nAChR activity. The compounds of the present invention may in particular be found to be agonists, partial agonists, antagonists or allosteric modulators of the receptor.

Due to their pharmacological profiles, compound of the invention are anticipated to be useful for the treatment of diseases or conditions as diverse as CNS related diseases, PNS related diseases, diseases related to inflammation, pain and withdrawal symptoms caused by an abuse of chemical substances. Diseases or disorders related to the CNS include general anxiety disorders, cognitive disorders, learning and memory deficits and dysfunctions, Alzheimer's disease (AD), prodromal AD, mild cognitive impairment in the elderly (MCI), amnestic MCI, age associated memory impairment, attention deficit and hyperactivity disorder (ADHD), Parkinson's disease, Huntington's disease, ALS, prionic neurodegenerative disorders such as Creutzfeld-Jacob disease and kuru disease, Gilles de la Tourette's syndrome, psychosis, depression and depressive disorders, mania, manic depression, schizophrenia, the cognitive deficits in schizophrenia, obsessive compulsive disorders, panic disorders, eating disorders, narcolepsy, nociception, AIDS-dementia, senile dementia, mild cognitive dysfunctions related to age, autism, dyslexia, tardive dyskinesia, epilepsy, and convulsive disorders, post-traumatic stress disorders, transient anoxia, pseudodementia, pre-menstrual syndrome, late luteal phase syndrome, chronic fatigue syndrome and jet lag. Furthermore, compound of the invention may be useful for the treatment of endocrine disorders, such as thyrotoxicosis, pheochromocytoma, hypertension and arrhythmias as well as angina pectoris, hyperkinesia, premature ejaculation and erectile difficulty. Still further, compound of the invention may be useful in the treatment of inflammatory disorders (Wang et al., Nature 2003, 421, 384; de Jonge et al., Nature Immunology 2005, 6, 844; Saeed et al., JEM 2005, 7, 1113), disorders or conditions including inflammatory skin disorders, rheumatoid arthritis, post-operative ileus, Crohn's diesease, inflammatory bowel disease, ulcerative colitis, sepsis, fibromyalgia, pancreatitis and diarrhoea. Compounds of the invention may further be useful for the treatment of withdrawal symptoms caused by termination of the use of addictive substances, like heroin, cocaine, tobacco, nicotine, opioids, benzodiazepines and alcohol. Finally, compound of the invention may be useful for the treatment of pain, e.g. caused by migraine, postoperative pain, phantom limb pain or pain associated with cancer. The pain may comprise inflammatory or neuropathic pain, central pain, chronic headache, pain related to diabetic neuropathy, to post therapeutic neuralgia or to peripheral nerve injury.

Furthermore, degenerative ocular disorders which may be treated include ocular diseases which may directly or indirectly involve the degeneration of retinal cells, including ischemic retinopathies in general, anterior ischemic optic neuropathy, all forms of optic neuritis, age-related macular degeneration (AMD), in its dry forms (dry AMD) and wet forms (wet AMD), diabetic retinopathy, cystoid macular edema (CME), retinal detachment, retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy.

It has been found that the effect of a combination which comprises at least one nicotinic-alpha 7 receptor agonist and at least one compound selected from the group consisting of (a) conventional antipsychotics and (b) atypical antipsychotics is greater than the additive effect of the combined drugs in the treatment of psychiatric disorders. In particular, the combinations disclosed herein can be used to treat schizophrenia which is refractory to monotherapy employing one of the combination partners alone.

Therefore, in one aspect of the present invention, there is provided a combination, such as a combined preparation or pharmaceutical composition, which comprises at least one nicotinic-alpha 7 receptor agonist and at least one compound selected from the group consisting of (a) conventional antipsychotics; and (b) atypical antipsychotics, in which the active ingredients are present in each case in free form or in the form of a pharmaceutically acceptable salt and optionally at least one pharmaceutically acceptable carrier.

Any such combuination may be administered for simultaneous, separate or sequential use.

The term "psychiatric disorders" as used herein includes, but is not limited to schizophrenia, anxiety disorders, depression and bipolar disorders. Preferably, the psychiatric disorder to be treated with the combination disclosed herein is schizophrenia, more preferably schizophrenia which is refractory to monotherapy employing one of the combination partners alone.

The term "conventional antipsychotics" as used herein includes, but is not limited to haloperidol, fluphenazine, thiotixene and flupentixol.

The term "atypical antipsychotics" as used herein includes, but is not limited to clozaril, risperidone, olanzapine, quetiapine, ziprasidone and aripiprazol.

In another aspect, the compounds of the invention are used as diagnostic agents and/or PET ligands and/or SPECT ligands, e.g. for the identification and localization of nicotine receptors in various tissues.

In particular, the agents of the invention are $\alpha 7$ nicotinic acetylcholine receptor ($\alpha 7$ nAChR) agonists.

In functional assays, the agents of the invention display high affinity at the $\alpha 7$ nAChR as shown in the following tests:

a) A functional assay for affinity at the $\alpha 7$ nAChR is carried out with a rat pituitary cell line stably expressing the $\alpha 7$ nAChR (Feuerbach et al., Neuropharmacology, 2005, 48, 215). Briefly, GH3 cells recombinantly expressing the nAChR $\alpha 7$ were seeded 72 h prior to the experiment on black 96-well plates and incubated at 37° C. in a humidified atmosphere (5% $CO_2$/95% air). On the day of the experiment medium was removed by flicking the plates and replaced with 100 µl growth medium containing of fluorescent calcium sensitive dye, in the presence of 2.5 mM probenicid (Sigma). The cells were incubated at 37° C. in a humidified atmosphere (5% $CO_2$/95% air) for 1 h. Plates were flicked to remove excess of Fluo-4, washed twice with Hepes-buffered salt solution (in mM: NaCl 130, KCl 5.4, $CaCl_2$ 2, $MgSO_4$ 0.8, $NaH_2PO_4$ 0.9, glucose 25, Hepes 20, pH 7.4; HBS) and refilled with 100 µl of HBS containing antagonists when appropriate. The incubation in the presence of the antagonist lasted between 3 and 5 minutes. Plates were then placed into an imaging plate reader and fluorescence signal recorded In this assay, compounds of the invention exhibit $pEC_{50}$ values of about 5 to about 9. Partial and potent agonists in this test are preferred.

b) To assess the antagonist activity of the compounds of the invention on the human neuronal nAChR $\alpha 4\beta 2$, a similar functional assay is carried out using a human epithelial cell line stably expressing the human $\alpha 4\beta 2$ subtype (Michelmore et al., Naunyn-Schmiedeberg's Arch. Pharmacol. (2002) 366, 235) In this assay, the preferred compounds of the invention show selectivity for the $\alpha 7$ nAChR subtypes.

c) To assess the antagonist activity of the compounds of the invention on the "ganglionic subtype" ($\alpha 3\beta 4$), the muscle type of nicotinic receptor ($\alpha 1\beta 1\gamma\delta$) and the $5-HT_3$ receptor, similar functional tests as just described under a) are carried out with a human epithelial cell line stably expressing the human ganglionic subtype, a cell line endogenously expressing the human muscle type of nicotinic receptors or a cell line endogenously expressing the murine $5-HT_3$ receptor (Michelmore et al., Naunyn-Schmiedeberg's Arch. Pharmacol. (2002) 366, 235. Compounds which display little or no activity on the $\alpha 3\beta 4$ nAChR, the muscle subtype of nicotinic receptor as well as the $5-HT_3$ receptor are especially preferred.

In the model of mice showing sensory gating deficit (DBA/2-mice) described by S. Leonard et al. in Schizophrenia Bulletin 22, 431-445 (1996), the compounds of the invention may induce significant sensory gating at concentrations of about 10 to about 40 µM.

The compounds of the invention may be shown to increase attention in a test of attention for rodents (Robbins, J. Neuropsychiatry Clin. Neurosci. (2001) 13, 326-35), namely the 5-choice serial reaction time test (5-CSRTT). In this test, the rat must observe a wall containing 5 holes. When a light flash appears in one of them, the rat must respond with a nose-poke into the correct hole within 5 sec. in order to receive a food pellet reward, delivered to a feeder in the opposite wall.

Compounds of the invention may also show learning/memory enhancing effects in the social recognition test in mice and rats (Ennaceur and Delacour, Behav. Brain Res. (1988) 31, 47-59).

Compounds of the invention may also show learning/memory enhancing effects in the object recognition test in mice and rats (Ennaceur and Delacour, Behav. Brain Res. (1988) 31, 47-59). The compounds of the invention are therefore useful for the prevention, treatment and delay of progression (including mitigation and prevention) of various disorders, especially those mentioned above. The usefulness of $\alpha 7$ nAChR agonists in neurodegeneration is documented in the literature, e.g. in Wang et al., J. Biol. Chem. 275, 5626-5632 (2000).

For the treatment of the above and other disorders, the appropriate dosage of a compound (active ingredient) of the invention will, of course, vary depending upon, for example, the host, the mode of administration and the nature and severity of the condition being treated as well as the relative potency of the particular agent of the invention employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 30.0 mg/kg p.o. In humans, an indicated daily dosage is in the range of from about 0.7 to about 1400 mg/day p.o., e.g. from about 50 to 200 mg (70 kg man), conveniently administered once or in divided doses up to 4×per day or in sustained release form.

Pharmaceutical compositions contain, for example, from about 0.1% to about 99.9%, preferably from about 20% to about 60%, of the active ingredient(s).

Examples for compositions comprising a compound of the invention include, for example, a solid dispersion, an aqueous solution, e.g. containing a solubilising agent, a microemulsion and a suspension of, e.g. a salt of a compound of formula (I) or a free compound of the formula (I) in the range of from 0.1 to 1%, e.g. 0.5%. The composition may be buffered to a pH in the range of, e.g. from 3.5 to 9.5, e.g. to pH 4.5, by a suitable buffer.

The compounds of the invention are also commercially useful as research chemicals.

For use according to the invention, a compound of the formula (I) and/or a pharmaceutically acceptable salt thereof may be administered as single active agent or in combination with one or more other active agents of the formula (I) and/or a pharmaceutically acceptable salt thereof or especially other active agents commonly employed especially for the treatment of the disorders mentioned herein or further other disorders, in any customary manner, e.g. orally, for example in the form of tablets, capsules, or as nasal spray, or parenterally, for example in the form of injection solutions or suspensions. Such other active agents employed in such combinations are preferably selected from the group consisting of benzodiazepines, selective serotonin reuptake inhibitors (SSRIs), selective serotonin and norepinephrine reuptake inhibitors (SNRIs), conventional antipsychotics, atypical antipsychotics, buspirone, carbamazepine, oxcarbazepine, gabapentin and pregabalin.

An SSRI suitable for the present invention is especially selected from fluoxetine, fuvoxamine, sertraline, paroxetine, citalopram and escitalopram. An SNRI suitable for the present invention is especially selected from venlafaxine and duloxetine. The term "benzodiazepines" as used herein includes, but is not limited to clonazepam, diazepam and lorazepam. The term "conventional antipsychotics" as used herein includes, but is not limited to haloperidol, fluphenazine, thiotixene and flupentixol. The term "atypical antipsychotics" as used herein relates to clozaril, risperidone, olanzapine, quetiapine, ziprasidone and aripiprazol.

Buspirone can be administered in free form or as a salt, e.g. as its hydrochloride, e.g., in the form as marketed, e.g. under the trademark Buspar™ or Bespar™. It can be prepared and administered, e.g., as described in U.S. Pat. No. 3,717,634. Fluoxetine can be administered, e.g., in the form of its hydrochloride as marketed, e.g. under the trademark Prozac™. It can be prepared and administered, e.g., as described in CA 2002182. Paroxetine ((3S,4R)-3-[(1,3-benzodioxol-5-yloxy)methyl]-4-(4-fluorophenyl)piperidine) can be administered, e.g., in the form as marketed, e.g. under the trademark Paxil™. It can be prepared and administered, e.g., as described in U.S. Pat. No. 3,912,743. Sertraline can be administered, e.g., in the form as marketed, e.g. under the trademark Zoloft™. It can be prepared and administered, e.g., as described in U.S. Pat. No. 4,536,518. Clonazepam can be administered, e.g., in the form as marketed, e.g. under the trademark Anteleosin™. Diazepam can be administered, e.g., in the form as marketed, e.g. under the trademark Diazepam Desitin™. Lorazepam can be administered, e.g., in the form as marketed, e.g. under the trademark Tavor™. Citalopram can be administered in free form or as a salt, e.g. as its hydrobromide, e.g., in the form as marketed, e.g. under the trademark Cipramil™. Escitalopram can be administered, e.g., in the form as marketed, e.g. under the trademark Cipralex™. It can be prepared and administered, e.g., as described in AU623144. Venlafaxine can be administered, e.g., in the form as marketed, e.g. under the trademark Trevilor™. Duloxetine can be administered, e.g., in the form as marketed, e.g. under the trademark Cymbalta™. It may be prepared and administered, e.g., as described in CA 1302421. Carbamazepine can be administered, e.g., in the form as marketed, e.g. under the trademark Tegretal™ or Tegretol™. Oxcarbazepine can be administered, e.g., in the form as marketed, e.g. under the trademark Trileptal™. Oxcarbazepine is well known from the literature [see for example Schuetz H. et al., Xenobiotica (GB), 16(8), 769-778 (1986)]. Gabapentin can be administered, e.g., in the form as marketed, e.g. under the trademark Neurontin™. Haloperidol can be administered, e.g., in the form as marketed, e.g. under the trademark Haloperidol STADA™. Fluphenazine can be administered, e.g., in the form of its dihydrochloride as marketed, e.g. under the trademark Prolixin™. Thiothixene can be administered, e.g., in the form as marketed, e.g. under the trademark Navane™. It can be prepared, e.g., as described in U.S. Pat. No. 3,310,553. Flupentixol can be administered for instance in the form of its dihydrochloride, e.g., in the form as marketed, e.g. under the trademark Emergil™ or in the form of its decanoate, e.g., in the form as marketed, e.g. under the trademark Depixol™. It can be prepared, e.g., as described in BP 925,538. Clozaril can be administered, e.g., in the form as marketed, e.g. under the trademark Leponex™. It can be prepared, e.g., as described in U.S. Pat. No. 3,539,573. Risperidone can be administered, e.g., in the form as marketed, e.g. under the trademark Risperdal™. Olanzapine can be administered, e.g., in the form as marketed, e.g. under the trademark Zyprexa™. Quetiapine can be administered, e.g., in the form as marketed, e.g. under the trademark Seroquel™. Ziprasidone can be administered, e.g., in the form as marketed, e.g. under the trademark Geodon™. It can be prepared, e.g., as described in GB 281,309. Aripiprazole can be administered, e.g., in the form as marketed, e.g. under the trademark Abilify™. It can be prepared, e.g., as described in U.S. Pat. No. 5,006,528.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

In the case of a combination, the pharmaceutical compositions for separate administration of the combination partners and/or those for administration in a fixed combination, i.e. a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application. When the combination partners employed are applied in the form as marketed as single drugs, their dosage and mode of administration can take place in accordance with the information provided on the packet leaflet of the respective marketed drug in order to result in the beneficial effect described herein, if not mentioned herein otherwise.

Pharmaceutical preparations for the combination therapy for enteral or parenteral administration are, for example, those in unit dosage forms, such as sugar-coated tablets, tablets, capsules or suppositories, or furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can instead with a single dosage unit also be reached by administration of a two or more dosage units.

In particular, a therapeutically effective amount of each of the combination partners may be administered simultaneously or sequentially and in any order, and the components may be administered separately (e.g. sequentially after fixed or variable periods of time), or as a fixed combination. For example, the method of treatment (including mitigation) of a disorder according to the invention may comprise (i) administration of the combination partner (a) (a compound of the present invention) in free or pharmaceutically acceptable salt form and (ii) administration of a combination partner (b) (e.g. a different compound of the present invention or an active ingredient of a different formula) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners can be administered separately at different times during the course of therapy or concurrently in divided or single combination forms. Furthermore, the term "administering" also encompasses the use of a pro-drug of a combination partner that convert in vivo to the combination partner as such. The instant invention is therefore to be understood as embracing all such regimes of simultaneous and/or alternating treatment and the term "administering" is to be interpreted accordingly.

The effective dosage of the combination partners employed may vary, for example depending on the particular compound or pharmaceutical composition employed, the mode of administration, the disorder being treated, and/or the severity of the disorder being treated. Thus, the dosage regimen is selected in accordance with a variety of factors including the route of administration, metabolism by and the renal and hepatic function of the patient. A physician, clinician or veterinarian of ordinary skill can readily determine and prescribe the effective amount of the single active ingredients required to prevent, mitigate, counter or arrest the disorder. Optimal precision in achieving concentration of the active ingredients within the range that yields efficacy without toxicity requires a regimen based on the kinetics of the active ingredients' availability to target sites.

In accordance with the foregoing, the present invention also provides:

(1) A compound of the formula (I), and/or a salt thereof, for use in the diagnostic or therapeutic treatment of a mammal, especially a human; especially for use as an alpha-7 receptor agonist, for example for use in the treatment (including mitigation) of any one or more disorders, especially of any one or more of the particular disorders set forth hereinbefore and hereinafter.

(2) A pharmaceutical composition comprising a compound of the formula (I), and/or a pharmaceutically acceptable salt thereof, as active ingredient together with a pharmaceutically acceptable diluent or carrier.

(2') A pharmaceutical composition for the treatment or prevention of a disorder in the treatment of which alpha-7 receptor activation plays a role or is involved and/or in which alpha-7 receptor activity is involved, especially any one or more of the disorders mentioned hereinbefore or hereinafter, comprising a compound of the formula (I), and/or a pharmaceutically acceptable salt thereof, and a pharmaceutically acceptable diluent or carrier.

(3) A method for the treatment of a disorder, especially any one or more of the particular disorders set forth hereinbefore, in a subject in need of such treatment, comprising administering a pharmaceutically effective amount of a compound of the formula (I), or a pharmaceutically acceptable salt thereof.

(3') A method for treating or preventing a disorder in the treatment of which alpha-7 receptor activation plays a role or is involved and/or in which alpha-7 receptor activity is involved, comprising administering to a mammal in need thereof a therapeutically effective amount of a compound of the formula (I), and/or a pharmaceutically acceptable salt thereof.

(4) The use of a compound of the formula (I), and/or a pharmaceutically acceptable salt thereof, for the manufacture of a medicament for the treatment or prevention of a disease or condition in the treatment of which alpha-7 receptor activation plays a role or is involved and/or in which alpha-7 receptor activity is involved, especially one or more of the disorders mentioned above.

(5) A method as defined above comprising co-administration, e.g. concomitantly or in sequence, of a therapeutically effective amount of an alpha-7 agonist of the formula (I), and/or a pharmaceutically acceptable salt thereof, and a second pharmaceutically active compound and/or a pharmaceutically acceptable salt thereof, said second pharmaceutically active compound and/or salt thereof being especially for use in the treatment of any one or more of the disorders set forth hereinbefore or hereinafter.

(6) A combination comprising a therapeutically effective amount of an alpha-7 agonist of the formula (I), and/or a pharmaceutically acceptable salt thereof, and a second pharmaceutically active compound and/or a pharmaceutically acceptable salt thereof, said second pharmaceutically active compound being especially for use or of use in the treatment of any one or more of the particular disorders set forth hereinbefore.

The Examples which follow serve to illustrate the invention without limiting the scope thereof.

The following abbreviations are used in the examples:
AcOEt ethyl acetate
aq. aqueous
DMF dimethylformamide
EtOH ethanol
FC flash chromatography
HV high vacuum
MeOH MeOH
RP-HPLC reversed-phase high performance liquid chromatography
rt room temperature
rac. racemate
soln. solution
TFA trifluoroacetic acid
THF tetrahydrofuran Temperatures are measured in degrees Celsius. Unless indicated otherwise, reactions are carried out at room temperature. The structure of final products, intermediates and starting materials is confirmed by standard analytical methods, e.g. microanalysis and spectroscopic characteristics (e.g. MS, IR, NMR).

EXAMPLE 1

Preparation of Rac.-trans-2-Methyl-1-aza-bicyclo [2.2.2]oct-3-yl)-(6-phenyl-pyridin-3-yl)-amine A solution of 2-methyl-1-aza-bicyclo[2.2.2]octan-3-one (1.33 g, 9.5 mmol), 6-phenyl-pyridin-3-ylamine (1.25 g, 7.3 mmol) and p-toluene sulfonic acid monohydrate (139 mg, 0.73 mmol) in toluene (40 ml) is heated under reflux for 18 hours using a Dean-Stark apparatus. The toluene is evaporated and the residue is dissolved in ethyl acetate and washed with brine. The organic layer is dried over anhydrous magnesium sulfate, filtered and evaporated to dryness, and the residual oil purified by silica gel column chromatography (eluent: EtOAc: $CH_3OH:NH_4OH$; 9:1:0.1) to afford [2-Methyl-1-aza-bicyclo[2.2.2]oct-(3Z)-ylidene]-(6-phenyl-pyridin-3-yl)-amine. A solution of $LiAlH_4$ (1.03 ml, 1 M) in THF is added to a solution of [2-Methyl-1-aza-bicyclo[2.2.2]oct-(3Z)-ylidene]-(6-phenyl-pyridin-3-yl)-amine (300 mg, 1.02 mmol) in THF (10 ml). The resulting mixture is stirred at room temperature for 18 hours and then quenched with a saturated aqueous solution of sodium sulfate (1 ml). The solvents are removed by evaporation and the residue is redissolved in ethyl acetate and filtered. The filtrate is evaporated and purified by silica gel column chromatography (eluent: EtOAc: $CH_3OH$: $NH_4OH$; 8.5:1.5:0.1) to afford Rac.-trans-2-Methyl-1-aza-bicyclo[2.2.2]oct-3-yl)-(6-phenyl-pyridin-3-yl)-amine. MS (ES$^+$): m/e=294.4 (MH$^+$); preparative enantiomer separation (column: Chiralpak AD-H 10 um; (4.6×250 mm), eluent: n-hexane : EtOH 50:50, flow: 1.0 ml/min, detector: UV 210 nm): peak 1: 6.29 min; peak 2: 20.16 min.

EXAMPLE 2

The following compounds are prepared in a similar manner using the appropriate starting materials:
2a) Rac.-trans-2-Methyl-1-aza-bicyclo[2.2.2]oct-3-yl)-(6-p-tolyl-pyridin-3-yl)-amine. MS (ES$^+$): m/e=308 (MH$^+$).
2b) Rac.-trans-(2-Methyl-1-aza-bicyclo[2.2.2]oct-3-yl)-(6-phenyl-pyridazin-3-yl)-amine
2c) Rac.-trans-(2-Methyl-1-aza-bicyclo[2.2.2]oct-3-yl)-(5-phenyl-pyridin-2-yl)-amine
2d) Rac.-trans-(2-Methyl-1-aza-bicyclo[2.2.2]oct-3-yl)-(5-phenyl-pyrimidin-2-yl)-amine

EXAMPLE 3

The following compounds are prepared in a similar manner using the appropriate starting materials:
3a) Rac.-trans-[6-(1H-Indol-5-yl)-pyridin-3-yl]-(2-methyl-1-aza-bicyclo[2.2.2]oct-3-yl)-amine; preparative enantiomer separation (column: Chiralpak AD 20 um; (50×500 mm), eluent: n-hexane : CHCl3 : EtOH 80:20, flow: 100 ml/min, detector: UV 200-400 nm): peak 1: 40.46 min; peak 2: 78.96 min.3b) Rac.-trans-[6-(1H-Indol-5-yl)-pyridazin-3-yl]-(2-methyl-1-aza-bicyclo[2.2.2]oct-3-yl)-amine
3c) Rac.-trans-[5-(1H-Indol-5-yl)-pyridin-2-yl]-(2-methyl-1-aza-bicyclo[2.2.2]oct-3-yl)-amine
3d) Rac.-trans-[5-(1H-Indol-5-yl)-pyrimidin-2-yl]-(2-methyl-1-aza-bicyclo[2.2.2]oct-3-yl)-amine
3e) Rac.-trans-(2-Methyl-1-aza-bicyclo[2.2.2]oct-3-yl)-[6-(5-methyl-thiophen-2-yl)-pyridin-3-yl]-amine
3f) Rac.-trans-(2-Methyl-1-aza-bicyclo[2.2.2]oct-3-yl)-[6-(5-methyl-thiophen-2-yl)-pyridazin-3-yl]-amine
3g) Rac.-trans-(2-Methyl-1-aza-bicyclo[2.2.2]oct-3-yl)-[5-(5-methyl-thiophen-2-yl)-pyridin-2-yl]-amine
3h) Rac.-trans-(2-Methyl-1-aza-bicyclo[2.2.2]oct-3-yl)-[5-(5-methyl-thiophen-2-yl)-pyrimidin-2-
3i) Rac.-trans-[6-(2,3-Dimethyl-1H-indol-5-yl)-pyridin-3-yl]-(2-methyl-1-aza-bicyclo[2.2.2]oct-3-yl)-amine
3j) Rac.-trans-[6-(2,3-Dimethyl-1H-indol-5-yl)-pyridazin-3-yl]-(2-methyl-1-aza-bicyclo[2.2.2]oct-3-yl)-amine
3k) Rac.-trans-[5-(2,3-Dimethyl-1H-indol-5-yl)-pyridin-2-yl]-(2-methyl-1-aza-bicyclo[2.2.2]oct-3-yl)-amine
3l) Rac.-trans-[5-(2,3-Dimethyl-1H-indol-5-yl)-pyrimidin-2-yl]-(2-methyl-1-aza-bicyclo[2.2.2]oct-3-yl)-amine
3m) Rac.-trans-[6-(1H-Indol-6-yl)-pyridin-3-yl]-(2-methyl-1-aza-bicyclo[2.2.2]oct-3-yl)-amine
3n) Rac.-trans-[6-(1H-Indol-6-yl)-pyridazin-3-yl]-(2-methyl-1-aza-bicyclo[2.2.2]oct-3-yl)-amine
3o) Rac.-trans-[5-(1H-Indol-6-yl)-pyridin-2-yl]-(2-methyl-1-aza-bicyclo[2.2.2]oct-3-yl)-amine
3p) Rac.-trans-[5-(1H-Indol-6-yl)-pyrimidin-2-yl]-(2-methyl-1-aza-bicyclo[2.2.2]oct-3-yl)-amine
3q) Rac.-trans-[6-(2,5-Difluoro-4-methyl-phenyl)-pyridin-3-yl]-(2-methyl-1-aza-bicyclo[2.2.2]oct-3-yl)-amine
3r) Rac.-trans-[6-(2,5-Difluoro-4-methyl-phenyl)-pyridazin-3-yl]-(2-methyl-1-aza-bicyclo[2.2.2]oct-3-yl)-amine
3s) Rac.-trans-[5-(2,5-Difluoro-4-methyl-phenyl)-pyridin-2-yl]-(2-methyl-1-aza-bicyclo[2.2.2]oct-3-yl)-amine
3t) Rac.-trans-[5-(2,5-Difluoro-4-methyl-phenyl)-pyrimidin-2-yl]-(2-methyl-1-aza-bicyclo[2.2.2]oct-3-yl)-amine
3u) 3q) Rac.-trans-[6-(2-fluoro-4-methyl-phenyl)-pyridin-3-yl]-(2-methyl-1-aza-bicyclo[2.2.2]oct-3-yl)-amine
3v) Rac.-trans-[6-(2-fluoro-4-methyl-phenyl)-pyridazin-3-yl]-(2-methyl-1-aza-bicyclo[2.2.2]oct-3-yl)-amine
3w) Rac.-trans-[5-(2-fluoro-4-methyl-phenyl)-pyridin-2-yl]-(2-methyl-1-aza-bicyclo[2.2.2]oct-3-yl)-amine
3x) Rac.-trans-[5-(2-fluoro-4-methyl-phenyl)-pyrimidin-2-yl]-(2-methyl-1-aza-bicyclo[2.2.2]oct-3-yl)-amine
3y) Rac.-trans-(2-Methyl-1-aza-bicyclo[2.2.2]oct-3-yl)-(6-m-tolyl-pyridin-3-yl)-amine
3z) Rac.-trans-(2-Methyl-1-aza-bicyclo[2.2.2]oct-3-yl)-(6-m-tolyl-pyridazin-3-yl)-amine
3aa) Rac.-trans-(2-Methyl-1-aza-bicyclo[2.2.2]oct-3-yl)-(5-m-tolyl-pyridin-2-yl)-amine
3ab) (2-Methyl-1-aza-bicyclo[2.2.2]oct-3-yl)-(5-m-tolyl-pyrimidin-2-yl)-amine
3ac) Rac.-trans-(2-Methyl-1-aza-bicyclo[2.2.2]oct-3-yl)-[6-(3-nitro-phenyl)-pyridin-3-yl]-amine
3ad) Rac.-trans-(2-Methyl-1-aza-bicyclo[2.2.2]oct-3-yl)-[6-(3-nitro-phenyl)-pyridazin-3-yl]-amine
3ae) Rac.-trans-(2-Methyl-1-aza-bicyclo[2.2.2]oct-3-yl)-[5-(3-nitro-phenyl)-pyridin-2-yl]-amine
3af) Rac.-trans-(2-Methyl-1-aza-bicyclo[2.2.2]oct-3-yl)-[5-(3-nitro-phenyl)-pyrimidin-2-yl]-amine
3ak) Rac.-trans-[6-(5-Ethyl-2-fluoro-phenyl)-pyridin-3-yl]-(2-methyl-1-aza-bicyclo[2.2.2]oct-3-yl)-amine
3al) Rac.-trans-[6-(5-Ethyl-2-fluoro-phenyl)-pyridazin-3-yl]-(2-methyl-1-aza-bicyclo[2.2.2]oct-3-yl)-amine
3am) Rac.-trans-[5-(5-Ethyl-2-fluoro-phenyl)-pyridin-2-yl]-(2-methyl-1-aza-bicyclo[2.2.2]oct-3-yl)-amine
3an) Rac.-trans-[5-(5-Ethyl-2-fluoro-phenyl)-pyrimidin-2-yl]-(2-methyl-1-aza-bicyclo[2.2.2]oct-3-yl)-amine
3ao) Rac.-trans-(6-Benzo[1,3]dioxol-5-yl-pyridin-3-yl)-(2-methyl-1-aza-bicyclo[2.2.2]oct-3-yl)-amine
3ap) Rac.-trans-(6-Benzo[1,3]dioxol-5-yl-pyridazin-3-yl)-(2-methyl-1-aza-bicyclo[2.2.2]oct-3-yl)-amine
3aq) Rac.-trans-(5-Benzo[1,3]dioxol-5-yl-pyridin-2-yl)-(2-methyl-1-aza-bicyclo[2.2.2]oct-3-yl)-amine
3ar) Rac.-trans-(5-Benzo[1,3]dioxol-5-yl-pyrimidin-2-yl)-(2-methyl-1-aza-bicyclo[2.2.2]oct-3-yl)-amine
3as) Rac.-trans-[6-(3-Methoxy-phenyl)-pyridin-3-yl]-(2-methyl-1-aza-bicyclo[2.2.2]oct-3-yl)-amine
3at) Rac.-trans-[6-(3-Methoxy-phenyl)-pyridazin-3-yl]-(2-methyl-1-aza-bicyclo[2.2.2]oct-3-yl)-amine
3au) Rac.-trans-[5-(3-Methoxy-phenyl)-pyridin-2-yl]-(2-methyl-1-aza-bicyclo[2.2.2]oct-3-yl)-amine
3av) Rac.-trans-[5-(3-Methoxy-phenyl)-pyrimidin-2-yl]-(2-methyl-1-aza-bicyclo[2.2.2]oct-3-yl)-amine
3bd) Rac.-trans-N-{4-[2-(2-Methyl-1-aza-bicyclo[2.2.2]oct-3-yloxy)-pyrimidin-5-yl]-phenyl}-acetamide
3be) Rac.-trans-[6-(2-Fluoro-5-methoxy-4-methyl-phenyl)-pyridin-3-yl]-(2-methyl-1-aza-bicyclo[2.2.2]oct-3-yl)-amine
3bf) Rac.-trans-[6-(2-Fluoro-5-methoxy-4-methyl-phenyl)-pyridazin-3-yl]-(2-methyl-1-aza-bicyclo[2.2.2]oct-3-yl)-amine
3bg) Rac.-trans-[5-(2-Fluoro-5-methoxy-4-methyl-phenyl)-pyridin-2-yl]-(2-methyl-1-aza-bicyclo[2.2.2]oct-3-yl)-amine
3bh) Rac.-trans-[5-(2-Fluoro-5-methoxy-4-methyl-phenyl)-pyrimidin-2-yl]-(2-methyl-1-aza-bicyclo[2.2.2]oct-3-yl)-amine
3bi) Rac.-trans-[6-(3,5-Dimethyl-phenyl)-pyridin-3-yl]-(2-methyl-1-aza-bicyclo[2.2.2]oct-3-yl)-amine; preparative enantiomer separation (column: Chiralpak AD-H 10 um; (4.6×250 mm), eluent: n-hexane : EtOH : DEA 50:50:0.5 (v:v:v), flow: 1.0 ml/min, detector: UV 220 nm): peak 1:

8.25 min; peak 2: 23.57 min.3bj) Rac.-trans-[6-(3,5-Dimethyl-phenyl)-pyridazin-3-yl]-(2-methyl-1-aza-bicyclo[2.2.2]oct-3-yl)-amine 3bk) Rac.-trans-[5-(3,5-Dimethyl-phenyl)-pyridin-2-yl]-(2-methyl-1-aza-bicyclo[2.2.2]oct-3-yl)-amine 3bl) Rac.-trans-[5-(3,5-Dimethyl-phenyl)-pyrimidin-2-yl]-(2-methyl-1-aza-bicyclo[2.2.2]oct-3-yl)-amine 3bm) Rac.-trans-(2-Methyl-1-aza-bicyclo[2.2.2]oct-3-yl)-[6-(1-methyl-1H-indol-5-yl)-pyridin-3-yl]-amine 3bn) Rac.-trans-(2-Methyl-1-aza-bicyclo[2.2.2]oct-3-yl)-[6-(1-methyl-1H-indol-5-yl)-pyridazin-3-yl]-amine 3bo) Rac.-trans-(2-Methyl-1-aza-bicyclo[2.2.2]oct-3-yl)-[5-(1-methyl-1H-indol-5-yl)-pyrimidin-2-yl]-amine 3bp) Rac.-trans-(2-Methyl-1-aza-bicyclo[2.2.2]oct-3-yl)-[5-(1-methyl-1H-indol-5-yl)-pyridin-2-yl]-amine 3bq) Rac.-trans-[6-(3,4-Difluoro-phenyl)-pyridin-3-yl]-(2-methyl-1-aza-bicyclo[2.2.2]oct-3-yl)-amine 3br) Rac.-trans-[6-(3,4-Difluoro-phenyl)-pyridazin-3-yl]-(2-methyl-1-aza-bicyclo[2.2.2]oct-3-yl)-amine 3bs) Rac.-trans-[5-(3,4-Difluoro-phenyl)-pyridin-2-yl]-(2-methyl-1-aza-bicyclo[2.2.2]oct-3-yl)-amine 3bt) Rac.-trans-[5-(3,4-Difluoro-phenyl)-pyrimidin-2-yl]-(2-methyl-1-aza-bicyclo[2.2.2]oct-3-yl)-amine 3bu) Rac.-trans-[6-(3,4-Dimethyl-phenyl)-pyridin-3-yl]-(2-methyl-1-aza-bicyclo[2.2.2]oct-3-yl)-amine 3bv) Rac.-trans-[6-(3,4-Dimethyl-phenyl)-pyridazin-3-yl]-(2-methyl-1-aza-bicyclo[2.2.2]oct-3-yl)-amine 3bw) Rac.-trans-[5-(3,4-Dimethyl-phenyl)-pyrimidin-2-yl]-(2-methyl-1-aza-bicyclo[2.2.2]oct-3-yl)-amine 3bx) Rac.-trans-[5-(3,4-Dimethyl-phenyl)-pyridin-2-yl]-(2-methyl-1-aza-bicyclo[2.2.2]oct-3-yl)-amine 3by) Rac.-trans-[6-(4-Fluoro-phenyl)-pyridin-3-yl]-(2-methyl-1-aza-bicyclo[2.2.2]oct-3-yl)-amine 3bz) Rac.-trans-[6-(4-Fluoro-phenyl)-pyridazin-3-yl]-(2-methyl-1-aza-bicyclo[2.2.2]oct-3-yl)-amine 3ca) Rac.-trans-[5-(4-Fluoro-phenyl)-pyridin-2-yl]-(2-methyl-1-aza-bicyclo[2.2.2]oct-3-yl)-amine 3cb) Rac.-trans-[5-(4-Fluoro-phenyl)-pyrimidin-2-yl]-(2-methyl-1-aza-bicyclo[2.2.2]oct-3-yl)-amine 3cc) Rac.-trans-(2-Methyl-1-aza-bicyclo[2.2.2]oct-3-yl)-[6-(3-trifluoromethoxy-phenyl)-pyridin-3-yl]-amine 3cd) Rac.-trans-(2-Methyl-1-aza-bicyclo[2.2.2]oct-3-yl)-[6-(3-trifluoromethoxy-phenyl)-pyridazin-3-yl]-amine 3ce) Rac.-trans-(2-Methyl-1-aza-bicyclo[2.2.2]oct-3-yl)-[5-(3-trifluoromethoxy-phenyl)-pyridin-2-yl]-amine 3cf) Rac.-trans-(2-Methyl-1-aza-bicyclo[2.2.2]oct-3-yl)-[5-(3-trifluoromethoxy-phenyl)-pyrimidin-2-yl]-amine 3cg) Rac.-trans-[6-(1H-Indol-4-yl)-pyridin-3-yl]-(2-methyl-1-aza-bicyclo[2.2.2]oct-3-yl)-amine 3ch) Rac.-trans-[6-(1H-Indol-4-yl)-pyridazin-3-yl]-(2-methyl-1-aza-bicyclo[2.2.2]oct-3-yl)-amine 3ci) Rac.-trans-[5-(1H-Indol-4-yl)-pyridin-2-yl]-(2-methyl-1-aza-bicyclo[2.2.2]oct-3-yl)-amine 3cj) Rac.-trans-[5-(1H-Indol-4-yl)-pyrimidin-2-yl]-(2-methyl-1-aza-bicyclo[2.2.2]oct-3-yl)-amine 3ck) Rac.-trans-[6-(4-Ethyl-phenyl)-pyridin-3-yl]-(2-methyl-1-aza-bicyclo[2.2.2]oct-3-yl)-amine 3cl) Rac.-trans-[6-(4-Ethyl-phenyl)-pyridazin-3-yl]-(2-methyl-1-aza-bicyclo[2.2.2]oct-3-yl)-amine 3cm) Rac.-trans-[5-(4-Ethyl-phenyl)-pyridin-2-yl]-(2-methyl-1-aza-bicyclo[2.2.2]oct-3-yl)-amine 3cn) Rac.-trans-[5-(4-Ethyl-phenyl)-pyrimidin-2-yl]-(2-methyl-1-aza-bicyclo[2.2.2]oct-3-yl)-amine 3co) Rac.-trans-[6-(3,4-Dimethoxy-phenyl)-pyridin-3-yl]-(2-methyl-1-aza-bicyclo[2.2.2]oct-3-yl)-amine 3cp) Rac.-trans-[6-(3,4-Dimethoxy-phenyl)-pyridazin-3-yl]-(2-methyl-1-aza-bicyclo[2.2.2]oct-3-yl)-amine 3cq) Rac.-trans-[5-(3,4-Dimethoxy-phenyl)-pyridin-2-yl]-(2-methyl-1-aza-bicyclo[2.2.2]oct-3-yl)-amine 3cr) Rac.-trans-[5-(3,4-Dimethoxy-phenyl)-pyrimidin-2-yl]-(2-methyl-1-aza-bicyclo[2.2.2]oct-3-yl)-amine 3cs) Rac.-trans-[6-(3-Fluoro-4-methyl-phenyl)-pyridin-3-yl]-(2-methyl-1-aza-bicyclo[2.2.2]oct-3-yl)-amine 3ct) Rac.-trans-[6-(3-Fluoro-4-methyl-phenyl)-pyridazin-3-yl]-(2-methyl-1-aza-bicyclo[2.2.2]oct-3-yl)-amine 3cu) Rac.-trans-[5-(3-Fluoro-4-methyl-phenyl)-pyridin-2-yl]-(2-methyl-1-aza-bicyclo[2.2.2]oct-3-yl)-amine 3cv) Rac.-trans-[5-(3-Fluoro-4-methyl-phenyl)-pyrimidin-2-yl]-(2-methyl-1-aza-bicyclo[2.2.2]oct-3-yl)-amine 3cw) Rac.-trans-[6-(2,5-Dimethoxy-phenyl)-pyridin-3-yl]-(2-methyl-1-aza-bicyclo[2.2.2]oct-3-yl)-amine 3cx) Rac.-trans-[6-(2,5-Dimethoxy-phenyl)-pyridazin-3-yl]-(2-methyl-1-aza-bicyclo[2.2.2]oct-3-yl)-amine 3cy) Rac.-trans-[5-(2,5-Dimethoxy-phenyl)-pyridin-2-yl]-(2-methyl-1-aza-bicyclo[2.2.2]oct-3-yl)-amine 3cz) Rac.-trans-[5-(2,5-Dimethoxy-phenyl)-pyrimidin-2-yl]-(2-methyl-1-aza-bicyclo[2.2.2]oct-3-yl)-amine 3da) Rac.-trans-[6-(3-Chloro-phenyl)-pyridin-3-yl]-(2-methyl-1-aza-bicyclo[2.2.2]oct-3-yl)-amine 3db) Rac.-trans-[6-(3-Chloro-phenyl)-pyridazin-3-yl]-(2-methyl-1-aza-bicyclo[2.2.2]oct-3-yl)-amine 3dc) Rac.-trans-[5-(3-Chloro-phenyl)-pyridin-2-yl]-(2-methyl-1-aza-bicyclo[2.2.2]oct-3-yl)-amine 3dd) Rac.-trans-[5-(3-Chloro-phenyl)-pyrimidin-2-yl]-(2-methyl-1-aza-bicyclo[2.2.2]oct-3-yl)-amine 3de) Rac.-trans-(6-Furan-3-yl-pyridin-3-yl)-(2-methyl-1-aza-bicyclo[2.2.2]oct-3-yl)-amine 3df) Rac.-trans-(6-Furan-3-yl-pyridazin-3-yl)-(2-methyl-1-aza-bicyclo[2.2.2]oct-3-yl)-amine 3dg) Rac.-trans-(5-Furan-3-yl-pyridin-2-yl)-(2-methyl-1-aza-bicyclo[2.2.2]oct-3-yl)-amine 3dh) Rac.-trans-(5-Furan-3-yl-pyrimidin-2-yl)-(2-methyl-1-aza-bicyclo[2.2.2]oct-3-yl)-amine 3di) Rac.-trans-(2-Methyl-1-aza-bicyclo[2.2.2]oct-3-yl)-[6-(4-methyl-thiophen-3-yl)-pyridin-3-yl]-amine 3dj) Rac.-trans-(2-Methyl-1-aza-bicyclo[2.2.2]oct-3-yl)-[6-(4-methyl-thiophen-3-yl)-pyridazin-3-yl]-amine 3dk) Rac.-trans-(2-Methyl-1-aza-bicyclo[2.2.2]oct-3-yl)-[5-(4-methyl-thiophen-3-yl)-pyridin-2-yl]-amine 3dl) Rac.-trans-(2-Methyl-1-aza-bicyclo[2.2.2]oct-3-yl)-[5-(4-methyl-thiophen-3-yl)-pyrimidin-2-yl]-amine 3dm) Rac.-trans-(2-Methyl-1-aza-bicyclo[2.2.2]oct-3-yl)-[6-(1-phenyl-1H-indol-5-yl)-pyridin-3-yl]-amine 3dn) Rac.-trans-(2-Methyl-1-aza-bicyclo[2.2.2]oct-3-yl)-[6-(1-phenyl-1H-indol-5-yl)-pyridazin-3-yl]-amine 3do) Rac.-trans-(2-Methyl-1-aza-bicyclo[2.2.2]oct-3-yl)-[5-(1-phenyl-1H-indol-5-yl)-pyridin-2-yl]-amine 3dp) Rac.-trans-(2-Methyl-1-aza-bicyclo[2.2.2]oct-3-yl)-[5-(1-phenyl-1H-indol-5-yl)-pyrimidin-2-yl]-amine 3dq) Rac.-trans-(2-Methyl-1-aza-bicyclo[2.2.2]oct-3-yl)-[6-(2-methyl-benzothiazol-5-yl)-pyridin-3-yl]-amine 3dr) Rac.-trans-(2-Methyl-1-aza-bicyclo[2.2.2]oct-3-yl)-[6-(2-methyl-benzothiazol-5-yl)-pyridazin-3-yl]-amine 3ds) Rac.-trans-(2-Methyl-1-aza-bicyclo[2.2.2]oct-3-yl)-[5-(2-methyl-benzothiazol-5-yl)-pyridin-2-yl]-amine 3dt) Rac.-trans-(2-Methyl-1-aza-bicyclo[2.2.2]oct-3-yl)-[5-(2-methyl-benzothiazol-5-yl)-pyrimidin-2-yl]-amine 3du) Rac.-trans-[6-(3,4-Dichloro-phenyl)-pyridin-3-yl]-(2-methyl-1-aza-bicyclo[2.2.2]oct-3-yl)-amine 3dv) Rac.-trans-[6-(3,4-Dichloro-phenyl)-pyridazin-3-yl]-(2-methyl-1-aza-bicyclo[2.2.2]oct-3-yl)-amine 3dw) Rac.-trans-[5-(3,4-Dichloro-phenyl)-pyridin-2-yl]-(2-methyl-1-aza-bicyclo[2.2.2]oct-3-yl)-amine 3dx) Rac.-trans-[5-(3,4-Dichloro-phenyl)-pyrimidin-2-yl]-(2-methyl-1-aza-bicyclo[2.2.2]oct-3-yl)-amine
3dy) Rac.-trans-[6-(2-Fluoro-phenyl)-pyridin-3-yl]-(2-methyl-1-aza-bicyclo[2.2.2]oct-3-yl)-amine
3dz) Rac.-trans-[6-(2-Fluoro-phenyl)-pyridazin-3-yl]-(2-methyl-1-aza-bicyclo[2.2.2]oct-3-yl)-amine
3ea) Rac.-trans-[5-(2-Fluoro-phenyl)-pyridin-2-yl]-(2-methyl-1-aza-bicyclo[2.2.2]oct-3-yl)-amine
3eb) Rac.-trans-[5-(2-Fluoro-phenyl)-pyrimidin-2-yl]-(2-methyl-1-aza-bicyclo[2.2.2]oct-3-yl)-amine
3ec) Rac.-trans-(2-Methyl-1-aza-bicyclo[2.2.2]oct-3-yl)-[6-(1H-pyrrolo[2,3-b]pyridin-5-yl)-pyridin-3-yl]-amine
3ed) Rac.-trans-(2-Methyl-1-aza-bicyclo[2.2.2]oct-3-yl)-[6-(1H-pyrrolo[2,3-b]pyridin-5-yl)-pyridazin-3-yl]-amine
3ee) Rac.-trans-(2-Methyl-1-aza-bicyclo[2.2.2]oct-3-yl)-[5-(1H-pyrrolo[2,3-b]pyridin-5-yl)-pyridin-2-yl]-amine
3ef) Rac.-trans-(2-Methyl-1-aza-bicyclo[2.2.2]oct-3-yl)-[5-(1H-pyrrolo[2,3-b]pyridin-5-yl)-pyrimidin-2-yl]-amine
3eg) Rac.-trans-(2-Methyl-1-aza-bicyclo[2.2.2]oct-3-yl)-(6-thiophen-2-yl-pyridin-3-yl)-amine
3eh) Rac.-trans-(2-Methyl-1-aza-bicyclo[2.2.2]oct-3-yl)-(6-thiophen-2-yl-pyridazin-3-yl)-amine
3ei) Rac.-trans-(2-Methyl-1-aza-bicyclo[2.2.2]oct-3-yl)-(5-thiophen-2-yl-pyridin-2-yl)-amine
3ej) Rac.-trans-(2-Methyl-1-aza-bicyclo[2.2.2]oct-3-yl)-(5-thiophen-2-yl-pyrimidin-2-yl)-amine
3ek) Rac.-trans-(6-Dibenzothiophen-4-yl-pyridin-3-yl)-(2-methyl-1-aza-bicyclo[2.2.2]oct-3-yl)-amine
3el) Rac.-trans-(6-Dibenzothiophen-4-yl-pyridazin-3-yl)-(2-methyl-1-aza-bicyclo[2.2.2]oct-3-yl)-amine
3em) Rac.-trans-(5-Dibenzothiophen-4-yl-pyridin-2-yl)-(2-methyl-1-aza-bicyclo[2.2.2]oct-3-yl)-amine
3en) Rac.-trans-(5-Dibenzothiophen-4-yl-pyrimidin-2-yl)-(2-methyl-1-aza-bicyclo[2.2.2]oct-3-yl)-amine
3eo) Rac.-trans-(6-Benzo[b]thiophen-3-yl-pyridin-3-yl)-(2-methyl-1-aza-bicyclo[2.2.2]oct-3-yl)-amine
3ep) Rac.-trans-(6-Benzo[b]thiophen-3-yl-pyridazin-3-yl)-(2-methyl-1-aza-bicyclo[2.2.2]oct-3-yl)-amine
3eq) Rac.-trans-(5-Benzo[b]thiophen-3-yl-pyridin-2-yl)-(2-methyl-1-aza-bicyclo[2.2.2]oct-3-yl)-amine
3er) Rac.-trans-(5-Benzo[b]thiophen-3-yl-pyrimidin-2-yl)-(2-methyl-1-aza-bicyclo[2.2.2]oct-3-yl)-amine
3es) Rac.-trans-(6'-Methoxy-[2,3']bipyridinyl-5-yl)-(2-methyl-1-aza-bicyclo[2.2.2]oct-3-yl)-amine
3et) Rac.-trans-[6-(6-Methoxy-pyridin-3-yl)-pyridazin-3-yl]-(2-methyl-1-aza-bicyclo[2.2.2]oct-3-yl)-amine
3eu) Rac.-trans-(6'-Methoxy-[3,3']bipyridinyl-6-yl)-(2-methyl-1-aza-bicyclo[2.2.2]oct-3-yl)-amine
3ev) Rac.-trans-[5-(6-Methoxy-pyridin-3-yl)-pyrimidin-2-yl]-(2-methyl-1-aza-bicyclo[2.2.2]oct-3-yl)-amine
3ew) Rac.-trans-[6-(1-Benzyl-1H-indol-5-yl)-pyridin-3-yl]-(2-methyl-1-aza-bicyclo[2.2.2]oct-3-yl)-amine
3ex) Rac.-trans-[6-(1-Benzyl-1H-indol-5-yl)-pyridazin-3-yl]-(2-methyl-1-aza-bicyclo[2.2.2]oct-3-yl)-amine
3ey) Rac.-trans-[5-(1-Benzyl-1H-indol-5-yl)-pyridin-2-yl]-(2-methyl-1-aza-bicyclo[2.2.2]oct-3-yl)-amine
3ez) Rac.-trans-[5-(1-Benzyl-1H-indol-5-yl)-pyrimidin-2-yl]-(2-methyl-1-aza-bicyclo[2.2.2]oct-3-yl)-amine
3fa) Rac.-trans-(6-Dibenzofuran-4-yl-pyridin-3-yl)-(2-methyl-1-aza-bicyclo[2.2.2]oct-3-yl)-amine
3fb) Rac.-trans-(6-Dibenzofuran-4-yl-pyridazin-3-yl)-(2-methyl-1-aza-bicyclo[2.2.2]oct-3-yl)-amine
3fc) Rac.-trans-(5-Dibenzofuran-4-yl-pyridin-2-yl)-(2-methyl-1-aza-bicyclo[2.2.2]oct-3-yl)-amine
3fd) Rac.-trans-(5-Dibenzofuran-4-yl-pyrimidin-2-yl)-(2-methyl-1-aza-bicyclo[2.2.2]oct-3-yl)-amine
3fe) Rac.-trans-[6-(2,3-Difluoro-4-methyl-phenyl)-pyridin-3-yl]-(2-methyl-1-aza-bicyclo[2.2.2]oct-3-yl)-amine
3ff) Rac.-trans-[6-(2,3-Difluoro-4-methyl-phenyl)-pyridazin-3-yl]-(2-methyl-1-aza-bicyclo[2.2.2]oct-3-yl)-amine
3fg) Rac.-trans-[5-(2,3-Difluoro-4-methyl-phenyl)-pyridin-2-yl]-(2-methyl-1-aza-bicyclo[2.2.2]oct-3-yl)-amine
3fh) Rac.-trans-[5-(2,3-Difluoro-4-methyl-phenyl)-pyrimidin-2-yl]-(2-methyl-1-aza-bicyclo[2.2.2]oct-3-yl)-amine
3fi) Rac.-trans-{6-[1-(4-Methoxy-phenyl)-1H-indol-5-yl]-pyridin-3-yl}-(2-methyl-1-aza-bicyclo[2.2.2]oct-3-yl)-amine
3fj) Rac.-trans-{6-[1-(4-Methoxy-phenyl)-1H-indol-5-yl]-pyridazin-3-yl}-(2-methyl-1-aza-bicyclo[2.2.2]oct-3-yl)-amine
3fk) Rac.-trans-{5-[1-(4-Methoxy-phenyl)-1H-indol-5-yl]-pyridin-2-yl}-(2-methyl-1-aza-bicyclo[2.2.2]oct-3-yl)-amine
3fl) Rac.-trans-{5-[1-(4-Methoxy-phenyl)-1H-indol-5-yl]-pyrimidin-2-yl}-(2-methyl-1-aza-bicyclo[2.2.2]oct-3-yl)-amine
3fm) Rac.-trans-[6-(4-Methoxy-phenyl)-pyridin-3-yl]-(2-methyl-1-aza-bicyclo[2.2.2]oct-3-yl)-amine
3fn) Rac.-trans-[6-(4-Methoxy-phenyl)-pyridazin-3-yl]-(2-methyl-1-aza-bicyclo[2.2.2]oct-3-yl)-amine
3fo) Rac.-trans-[5-(4-Methoxy-phenyl)-pyridin-2-yl]-(2-methyl-1-aza-bicyclo[2.2.2]oct-3-yl)-amine
3fp) Rac.-trans-[5-(4-Methoxy-phenyl)-pyrimidin-2-yl]-(2-methyl-1-aza-bicyclo[2.2.2]oct-3-yl)-amine
3fq) Rac.-trans-(6-Biphenyl-4-yl-pyridin-3-yl)-(2-methyl-1-aza-bicyclo[2.2.2]oct-3-yl)-amine
3fr) Rac.-trans-(6-Biphenyl-4-yl-pyridazin-3-yl)-(2-methyl-1-aza-bicyclo[2.2.2]oct-3-yl)-amine
3fs) Rac.-trans-(5-Biphenyl-4-yl-pyridin-2-yl)-(2-methyl-1-aza-bicyclo[2.2.2]oct-3-yl)-amine
3ft) Rac.-trans-(5-Biphenyl-4-yl-pyrimidin-2-yl)-(2-methyl-1-aza-bicyclo[2.2.2]oct-3-yl)-amine
3fu) Rac.-trans-(2-Methyl-1-aza-bicyclo[2.2.2]oct-3-yl)-[6-(3-trifluoromethyl-phenyl)-pyridin-3-yl]-amine
3fv) Rac.-trans-(2-Methyl-1-aza-bicyclo[2.2.2]oct-3-yl)-[6-(3-trifluoromethyl-phenyl)-pyridazin-3-yl]-amine
3fw) Rac.-trans-(2-Methyl-1-aza-bicyclo[2.2.2]oct-3-yl)-[5-(3-trifluoromethyl-phenyl)-pyridin-2-yl]-amine
3fX) Rac.-trans-(2-Methyl-1-aza-bicyclo[2.2.2]oct-3-yl)-[5-(3-trifluoromethyl-phenyl)-pyrimidin-2-yl]-amine
3fy) Rac.-trans-(2-Methyl-1-aza-bicyclo[2.2.2]oct-3-yl)-(6-quinolin-5-yl-pyridin-3-yl)-amine
3fz) Rac.-trans-(2-Methyl-1-aza-bicyclo[2.2.2]oct-3-yl)-(6-quinolin-5-yl-pyridazin-3-yl)-amine
3ga) Rac.-trans-(2-Methyl-1-aza-bicyclo[2.2.2]oct-3-yl)-(5-quinolin-5-yl-pyridin-2-yl)-amine
3gb) Rac.-trans-(2-Methyl-1-aza-bicyclo[2.2.2]oct-3-yl)-(5-quinolin-5-yl-pyrimidin-2-yl)-amine
3gc) Rac.-trans-[6-(2,2-Difluoro-benzo[1,3]dioxol-5-yl)-pyridin-3-yl]-(2-methyl-1-aza-bicyclo[2.2.2]oct-3-yl)-amine
3gd) Rac.-trans-[6-(2,2-Difluoro-benzo[1,3]dioxol-5-yl)-pyridazin-3-yl]-(2-methyl-1-aza-bicyclo[2.2.2]oct-3-yl)-amine
3ge) Rac.-trans-[5-(2,2-Difluoro-benzo[1,3]dioxol-5-yl)-pyridin-2-yl]-(2-methyl-1-aza-bicyclo[2.2.2]oct-3-yl)-amine
3gf) Rac.-trans-[5-(2,2-Difluoro-benzo[1,3]dioxol-5-yl)-pyrimidin-2-yl]-(2-methyl-1-aza-bicyclo[2.2.2]oct-3-yl)-amine
3gg) Rac.-trans-(6-Benzo[b]thiophen-2-yl-pyridin-3-yl)-(2-methyl-1-aza-bicyclo[2.2.2]oct-3-yl)-amine 3gh) Rac.-trans-(6-Benzo[b]thiophen-2-yl-pyridazin-3-yl)-(2-methyl-1-aza-bicyclo[2.2.2]oct-3-yl)-amine
3gi) Rac.-trans-(5-Benzo[b]thiophen-2-yl-pyridin-2-yl)-(2-methyl-1-aza-bicyclo[2.2.2]oct-3-yl)-amine
3gj) Rac.-trans-(5-Benzo[b]thiophen-2-yl-pyrimidin-2-yl)-(2-methyl-1-aza-bicyclo[2.2.2]oct-3-yl)-amine
3gk) Rac.-trans-[6-(1H-Indol-2-yl)-pyridin-3-yl]-(2-methyl-1-aza-bicyclo[2.2.2]oct-3-yl)-amine
3gl) Rac.-trans-[6-(1H-Indol-2-yl)-pyridazin-3-yl]-(2-methyl-1-aza-bicyclo[2.2.2]oct-3-yl)-amine
3gm) Rac.-trans-[5-(1H-Indol-2-yl)-pyridin-2-yl]-(2-methyl-1-aza-bicyclo[2.2.2]oct-3-yl)-amine
3gn) Rac.-trans-[5-(1H-Indol-2-yl)-pyrimidin-2-yl]-(2-methyl-1-aza-bicyclo[2.2.2]oct-3-yl)-amine
3go) Rac.-trans-5-[5-(2-Methyl-1-aza-bicyclo[2.2.2]oct-3-ylamino)-pyridin-2-yl]-thiophene-2-carbonitrile
3gp) Rac.-trans-5-[6-(2-Methyl-1-aza-bicyclo[2.2.2]oct-3-ylamino)-pyridazin-3-yl]-thiophene-2-carbonitrile
3gq) Rac.-trans-5-[6-(2-Methyl-1-aza-bicyclo[2.2.2]oct-3-ylamino)-pyridin-3-yl]-thiophene-2-carbonitrile
3gr) Rac.-trans-5-[2-(2-Methyl-1-aza-bicyclo[2.2.2]oct-3-ylamino)-pyrimidin-5-yl]-thiophene-2-carbonitrile
3gs) Rac.-trans-[6-(4-Methanesulfonyl-phenyl)-pyridin-3-yl]-(2-methyl-1-aza-bicyclo[2.2.2]oct-3-yl)-amine
3gt) Rac.-trans-[6-(4-Methanesulfonyl-phenyl)-pyridazin-3-yl]-(2-methyl-1-aza-bicyclo[2.2.2]oct-3-yl)-amine
3gu) Rac.-trans-[5-(4-Methanesulfonyl-phenyl)-pyridin-2-yl]-(2-methyl-1-aza-bicyclo[2.2.2]oct-3-yl)-amine
3gv) Rac.-trans-[5-(4-Methanesulfonyl-phenyl)-pyrimidin-2-yl]-(2-methyl-1-aza-bicyclo[2.2.2]oct-3-yl)-amine
3gw) Rac.-trans-[6-(4-Chloro-phenyl)-pyridin-3-yl]-(-2-methyl-1-aza-bicyclo[2.2.2]oct-3-yl)-amine; preparative enantiomer separation (column: Chiralcel OD-H 5 um; (4.6×250 mm), solvent A: n-hexane : EtOH 95:5 (v:v) +0.1% DEA, solvent B: EtOH, solvent composition: 85% A, 15% B (v:v), flow: 1.0 ml/min, detector: UV 270 nm): peak 1: 7.85 min; peak 2: 17.56 min.

EXAMPLE 4

(2,4-dimethoxy-benzyl)-(2-methyl-1-aza-bicyclo[2.2.2]oct-3-yl)-(5-phenyl-pyrimidin-2-yl)-amine 2-Methyl-1-aza-bicyclo[2.2.2]octan-3-one (500 mg, 3.59 mmol) and 2,4-dimethoxybenzyl amine (1.2 g, 7.18 mmol) were dissolved in anhydrous 1,2-dichloroethane (10 ml). Sodium triacetoxyborohydride (1.1 g, 5.0 mmol) followed by glacial acetic acid (0.21 ml, 3.59 mmol) and the resultant foamy suspension was stirred at ambient temperature for 12 hours. The reaction was quenched by the addition of 1M NaOH, and the layers were separated. The aqueous phase was extracted further with ethyl acetate. The organic portions were combined, dried ($Na_2SO_4$), filtered and concentrated in vacuo. The crude reaction mixture was purified by chromatography [eluent gradient: 10-30% MeOH/$Et_3N$ (9:1) in EtOAc) to give pure (2,4-dimethoxy-benzyl)-(2-methyl-1-aza-bicyclo[2.2.2]oct-3-yl)-amine.

(2,4-Dimethoxy-benzyl)-(2-methyl-1-aza-bicyclo[2.2.2]oct-3-yl)-amine (70 mg, 0.24 mmol) and 5-bromo chloropyrimidine (93 mg, 0.48 mmol) were dissolved in 1,4-dioxane (1 ml). Glacial acetic acid (42 □L, 0.72 mmol) was added and the reaction mixture was stirred under microwave radiation at 150° C. for 30 minutes. The reaction mixture was concentrated in vacuo, redissolved in EtOAc and washed with 1M aqueous sodium carbonate. The organic phase was dried ($Na_2SO_4$), filtered and concentrated in vacuo. The crude reaction mixture was purified by chromatography [eluent gradient: 10-30% MeOH/$Et_3N$ (9:1) in EtOAc) to give pure (5-bromo-pyrimidin-2-yl)-(2,4-dimethoxy-benzyl)-(2-methyl-1-aza-bicyclo[2.2.2]oct-3-yl)-amine.

(5-Bromo-pyrimidin-2-yl)-(2,4-dimethoxy-benzyl)-(2-methyl-1-aza-bicyclo[2.2.2]oct-3-yl)-amine (30 mg, 66 □mol), palladium(II) acetate (1 mg, 3.2 □mol), potassium fluoride (12 mg, 198 □mol) and 2-(di-t-butylphosphino)biphenyl (1.6 mg, 6.4 □mol) were combined and purged three times with argon and vacuum. Anhydrous THF (1 ml) was added and the reaction mixture stirred stirred under microwave radiation at 110° C. for 40 minutes. The crude reaction mixture was applied directly to a silica gel column and chromatographed [eluent gradient: 5-20% MeOH/$Et_3N$ (9:1) in EtOAc) to give pure (2,4-dimethoxy-benzyl)-(2-methyl-1-aza-bicyclo[2.2.2]oct-3-yl)-(5-phenyl-pyrimidin-2-yl)-amine. MS ($ES^+$): m/e=445.3 ($MH^+$).

EXAMPLE 5

Soft Capsules 5000 soft gelatin capsules, each comprising as active ingredient 0.05 g of one of the compounds of formula (I) mentioned in the preceding Examples, are prepared as follows:

Composition: Active ingredient: 250 g, Lauroglycol : 2 liters

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:
1. A compound of formula (I)

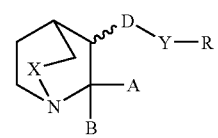

(I)

wherein
X represents $CH_2$,
R represents indolyl or substituted indolyl, the substituents being selected from the group consisting of halogen, cyano, $C_1$-$C_4$alkyl, $C_1$-$C_4$alkoxy, $C_1$-$C_4$halogenalkyl and phenyl;
Y represents one of the following groups:

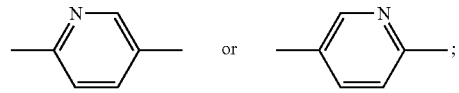

D represents NH;
A is methyl; and
B is hydrogen;
in free base or acid addition salt form.
2. A compound of claim 1 in pharmaceutically acceptable acid addition salt form.
3. A pharmaceutical composition comprising a compound of claim 1 in free base or pharmaceutically acceptable acid addition salt form, in association with a pharmaceutically acceptable carrier or diluent.

4. A compound of formula (I) according to claim 1 wherein said compound is racemic trans-[6-(1H-indol-5-yl)-pyridin-3-yl]-(2-methyl-1-aza-bicyclo[2.2.2]oct-3-yl)-amine in free base or pharmaceutically acceptable acid addition salt form.

5. A compound of claim 4 in pharmaceutically acceptable acid addition salt form.

6. A pharmaceutical composition comprising a compound of claim 4 in pharmaceutically acceptable acid addition salt form, in association with a pharmaceutically acceptable carrier or diluent.

7. A compound of claim 4 in free base form.

8. A pharmaceutical composition comprising a compound of claim 4 in free base form, in association with a pharmaceutically acceptable carrier or diluent.

9. A compound of claim 1 in free base form.

10. A pharmaceutical composition comprising a compound of claim 1 in free base form, in association with a pharmaceutically acceptable carrier or diluent.

11. A pharmaceutical composition comprising a compound of claim 1 in pharmaceutically acceptable acid addition salt form, in association with a pharmaceutically acceptable carrier or diluent.

* * * * *